United States Patent [19]
Kun et al.

[11] Patent Number: 5,484,951
[45] Date of Patent: Jan. 16, 1996

[54] 5-IODO-6-AMINO-6-NITROSO-1,2-BENZOPYRONES USEFUL AS CYTOSTATIC AND ANTIVIRAL AGENTS

[75] Inventors: Ernest Kun, Mill Valley; Jerome Mendeleyev, San Francisco, both of Calif.

[73] Assignee: Octamer, Incorporated, Mill Valley, Calif.

[21] Appl. No.: 600,593

[22] Filed: Oct. 19, 1990

[51] Int. Cl.$^6$ .................................................. C07D 311/02
[52] U.S. Cl. .......................... 549/285; 549/288; 549/289
[58] Field of Search ............................ 514/457; 549/285, 549/288, 289

[56] References Cited

U.S. PATENT DOCUMENTS

| | | | |
|---|---|---|---|
| 3,974,289 | 8/1976 | Buckle et al. | 514/457 |
| 4,012,407 | 3/1977 | Doyle et al. | 549/285 |
| 4,032,544 | 6/1977 | Doyle et al. | 549/285 |
| 4,737,517 | 4/1988 | della Valle et al. | 549/289 |
| 4,845,121 | 7/1989 | Witiak et al. | 514/457 |

FOREIGN PATENT DOCUMENTS

| | | |
|---|---|---|
| 3-227923 | 1/1990 | Japan . |
| 2036017 | 6/1980 | United Kingdom . |
| 2244646 | 11/1991 | United Kingdom . |
| WO89/07441 | 8/1989 | WIPO . |
| WO89/07939 | 9/1989 | WIPO . |
| WO89/09777 | 10/1989 | WIPO . |

OTHER PUBLICATIONS

Stuart-Harris, *The Background to Chemotherapy of Virus Diseases*, pp. 76–77, Charles C. Thomas publisher, Springfield, Ill. 1966.

Rice, W. et al., "Induction of endonuclease–mediated apoptosis in tumor cells by C–nitroso–substituted ligands of poly (ADP–ribose) polymerase." Proc. Natl. Acad. Sci. 89 7703–7707 (1992).

Buki, K. et al., "Destabilization of $Zn^{2+}$ coordination in ADP–ribose transferase (polymerizing) by C–nitroso–1, 2–benzopyrone coincidental with inactivation of the polymerase but not the DNA binding function." FEBS 290: 181–185 (1991).

Kirsten, E. et al., "Cellular regulation of ADP–ribosylation of proteins IV. Conversion of poly (ADP-Ribose) polymerase activity to NAD–glycohydrolase during retinoic acid–induced differentiation of HL60 cells." Experimental Cell Research 194:1–8 (1991).

Buki, K. et al., "Inhibitor binding of adenosine disphosphoribosyl transferase to the DNA primer site of reverse transcriptase templates." Biochem. Biophys. Res. Com. 180:496–503 (1991).

Henderson, L. et al., "Primary structure of the low molecular weight nucleic acid–binding proteins of murine leukemia viruses" J. Biol. Chem. 256(16) 8400–8403 (1981).

Gorelick, R. et al., "Point mutants of moloney murine leukemia virus that fail to package viral RNA: evidence for specific RNA recognition by a zinc–finger like protein sequence." Proc. Natl. Acad. Sci. 85:8420–8424 (1988).

Gorelick, R. et al., "Noninfectious human immunodeficiency virus Type 1 mutants deficient in genomic RNA." J. Virol. 64:3207–3211 (1990).

Meric, C. et al., "Characterization of moloney murine leukemia virus mutants with single amino acid substitutions in the Cys-His box of the nucleocapsid protein." J. Virol. 63:1558–1568 (1989).

Aldovini, A. et al., "Mutations of RNA and protein sequences involved in human immunodeficiency virus Type I packaging result in production of noninfectious virus." J. Virol. 64:1920–1926 (1990).

Lever, A. et al., "Identification of a sequence required for efficient packaging of human immunodeficiency virus Type I RNA into virions." J. Virol 63:4085–4087 (1989).

Gradwohl, G. et al., "The second zinc–finger domain of poly (ADP–ribose) polymerase determines specificity for single–stranded breaks in DNA." Proc. Natl. Acad. Sci. 87 2990–2994 (1990).

South, T. et al., "113 Cd NMR studies of 1:1 Cd adduct with an 18–residue finger peptide from HIV-1 nucleic acid binding protein, p7." J. Am. Chem. Soc. 111 395–396 (1989).

South, T. et al., "Zinc fingers and molecular recognition. Structure and nucleic acid binding studies of an HIV zinc fingerlike domain." Biochem. Pharm. 40:123–129 (1990).

Summers, M. et al., "High–resolution structure of an HIV zinc fingerlike domain via a new NMR–based distance geometry approach." Biochemistry 29:329–340 (1990).

Krasil'Nikov, I. et al., "Inhibitors of ADP–ribosylation as antiviral drugs: Experimental study of the model of HIV infection." VOPR.VIRUSOL (Russia) 36(3) 216–218 (1991).

Furlini, G. et al., "Increased poly (ADP–ribose) polymerase activity in cells infected by human immunodeficiency virus type–1." Microbiologica 14(2) 141–148 (1991).

Ibne–Rasa, K. et al., "O–Nitrosobenzamide. A possible intermediate in the von Richter reaction." J. Org. Chem. 47(24) 4664–4670 (1982).

Seidel, W. et al., "Oxidation of aromatic hydrazides." Chemical Abstracts 82 Col. 16505X (1975).

Wubbels,, G. et al., "Mechanism of water–catalyzed photo–isomerization of p–nitrobenzaldehyde." J. Org. Chem. 47(24) 4664–4670 (1982).

Kovacic, P. et al., "Reduction potentials in relation to physiological activities of benzenoid and heterocyclic nitroso compounds: comparison with the nitro precursors." Bioorganic Chemistry 18:265–275 (1990).

(List continued on next page.)

*Primary Examiner*—C. Warren Ivy
*Assistant Examiner*—A. Owens
*Attorney, Agent, or Firm*—Pennie & Edmonds

[57] ABSTRACT

Unsubstituted or substituted 5-iodo-6-amino-1,2-benopyrones and their metabolites are potent, selective and nontoxic inhibitors and suppressants of cancer growth and viral infections in a mammalian host. The compounds are particularly useful for treatment and suppression of tumors and viruses associated with AIDS, herpetic episodes and cytomegaloviral infections. The methods of treatment of tumorigenic and viral diseases by 5-iodo-6-amino-1,2-benzopyrones and/or its metabolites are described.

9 Claims, 6 Drawing Sheets

OTHER PUBLICATIONS

Ehlhardt, W. J. et al., "Nitrosoimidazoles: highly bactericidal analogues of 5-nitroimidazole drugs," J. Med. Chem. 31:323–329 (1988).

McClelland, R. A. et al., "Products of the reductions of 2-nitroimidazoles." J. Am. Chem. Soc. 109:4308–4314 (1987).

Noss, M. B. et al., "Preparation, toxicity and mutagenicity of 1-methyl-2-nitrosoimidazole." Biochem. Pharm. 37:2585–2593 (1988).

Varghese, A. J. et al., "Modification of guanine derivatives by reduced 2-nitroimidazoles." Cancer Research 43:78–82 (1983).

Buki, K. et al., "Destabilization of Zn(II) coordination in poly (ADP–Ribose) polymerase by 6-nitroso-1,2-benzopyrone coincidental with inactivation of the polymerase but not with the DNA binding function." The Paul Mandel International Meeting of Poly (ADP–Ribosyl)ation Reactions. Abstract 22C May 30, 1991.

Mulcahy, R. T. et al., "Cytotoxicity and glutathione depletioni by I-methyl-2-nitrosoimidazole in human colon cancer cells." Biochem. Pharm. 38:1667–1671 (1989).

Noss, M. B. et al., "I-Methyl-2-nitrosoimidazole: cytotoxic and glutathione depleting capabilities." Int. J. Radiation Oncology Biol. Phys. 16:1015–1019 (1989).

A "Inhibition of HIV-1 IIIb Replication in AA-2 and MT-2 Cells in Culture by Two Ligands of Poly (ADP–Ribose) Polymerase: 6-Amino-1,2-Benzopyrone and 5-IODO-6-Amino-1,2-Benzopyrone" Cole, Gerald A., et al. Biomed. and Biophys. Research Communications 180:504–514 (1991).

A Hakam, A. et al., "Catalytic activities of synthetic octa-deoxyribonucleotides as coenzymes of poly(ADP–ribose) polymerase and the identification of a new enzyme inhibitory site", FEBS Letters 212(1):73–78 (1987).

5-IODO-6-AMINO-6-NITROSO-1,2-BENZOPYRONES USEFUL AS CYTOSTATIC AND ANTIVIRAL AGENTS

The present invention was made in the course of research supported by the U.S. Department of Defense, Air Force Office of Scientific Research Grants AFOSR-89-0231. The U.S.Government may have rights in this invention.

BACKGROUND OF THE INVENTION

1. Field of the Invention

The present invention relates generally to novel 5-iodo-6-amino-1,2-benzopyrones and their metabolites, very potent, selective and safe cytostatic and antiviral agents, and to a method of treatment of tumorigenic and viral diseases using 5-iodo-6-amino-1,2-benzopyrones and their metabolites. More specifically, it relates to the use of 5-iodo-6-amino-1,2-benzopyrones, their homologues and salts, in suppressing and inhibiting the tumorous and metastatic growth and the growth of certain viruses in a mammalian host.

2. The State of Art and Related Disclosures

Both tumorigenic growth and viral infections become a most serious threat to modern society. Malignant cancerous growths became, due to their unique characteristics, one of the most serious diseases encountered by modern medicine. These characteristics are: uncontrollable cell proliferation which results in unregulated growth of malignant tissue, lack of differentiation and ability to invade local and even remote tissues, lack of detectable symptoms and the last but not the least, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation.

The above is particularly true in view of extreme secondary side effects found to be accompanying all currently available forms of cancer therapy. The success of surgery, the most radical treatment, depends on the stage when the cancer growth is discovered. If the whole tumor is discovered and removed before the metastases develop, then the surgery is effective. In the majority of cases, however, the cancer is discovered too late for surgery to be effective as the only treatment. Two other available therapies, such as radiotherapy, or chemotherapy are accompanied by severe adverse reactions. For radiation, sublethal doses are often required which directly affect the cell content and function.

Antineoplastic chemotherapy currently encompasses several groups of drugs. Alkylating agents alkylate cell proteins and nucleic acids thus preventing cell replication, disrupt the cell metabolism and lead to a cell death. Typical alkylating agents are nitrogen mustard, cyclophosphamide and chlorambucil. Toxicities associated with alkylating agents treatment include nausea, vomiting, alopecia, hemorrhagic cystitis, pulmonary fibrosis and an increased risk of development of acute leukemia. Purine, pyrimidine and folate antagonists are cell cycle and phase specific and, in order to promote anti-tumor effect, they require cells to be in the cell replication cycle and in the DNA synthesis phase of replication. The purine antagonists such as 6-mercaptopurine or 6-thioguanidine inhibit de novo purine synthesis and interconversion of purines. The pyrimide antagonists, such as cytarabine, 5-fluorouracil or floxuridine inhibit DNA synthesis by inhibiting deoxycytidylate kinase and DNA polymerase. Folate antagonists, methotrexates bind tightly with the intracellular enzyme dihydrofolate reductase, ultimately causing cell death from inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and dactinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutical treatment of cancer are inorganic ions such as cisplatin, biologic response modifiers such as interferon, enzymes and hormones. All these compounds, similarly to those mentioned above, are accompanied by toxic adverse reactions and consequently their use, as those others, is either limited or causes severe side effects.

Thus, it would be extremely advantageous to provide chemotherapeutic treatment which would effectively inhibit cancer cell proliferation and suppress neoplastic growth and would, at the same time be safe and non-toxic (*The Merck Manual*, 1218–1225 (1987), 15th Ed.). Novel compounds of this invention provide such treatment.

Similarly, the high degree of infectiousness and a fast reproduction cycle of viruses within the host organism, combined with essentially no effective treatment available aside from largely toxic deoxyribonucleotide homologs, make the viruses a nuisance and health hazard which the human population encounters on daily basis.

Viruses generally are very resistant to any treatment and some of them, for example herpes simplex viruses or cytomegalovirus, once inside the body, may remain forever in a dormant state until the resistance is weakened. The others, such as human immunodeficiency viruses are nearly always fatal.

There is no simple treatment of viral diseases. They are not susceptible to antibiotics and there is no other available treatment of viral diseases other than by chemotherapy which inhibits viral replication in the host cells (*The Merck Manual*, 170 (1982), 14th Ed.). Examples of these chemical agents are idoxuridine useful for treatment of herpes simplex keratitis and known viral replication inhibitors acyclovir, ribavirin, vidarabine, gancyclovir, adenine arabinoside (ARA-A) and AZT. These, and other viral replication inhibitors, however, are known to be cytotoxic, hepatotoxic, neurotoxic, nephrotoxic and were shown to have teratogenic effects (*Virus Diseases*, 1–6 (1978), Crown Publishers, N.Y.).

Thus it would be highly desirable to have available an effective and yet nontoxic treatment of viral diseases.

Human immunodeficiency virus (HIV) infections known as acquired immunodeficiency syndrome (AIDS), presently constitute one of, if not the most, pressing health hazards worldwide. HIV infections are almost always fatal due to a weakened immunoresistance, and due to accompanying opportunistic infections, malignancies and neurologic lesions leading to an early death.

There is no effective treatment for AIDS other than the treatment of the opportunistic infections, neoplasms and other complications. Available cytostatic (AZT) and antiviral (acyclovir) drugs are extremely toxic and cause severe adverse reactions. The most promising of all currently investigated drugs seem to be antivirals which may somehow inhibit the viral reproduction enzyme, reverse transcriptase (*The Merck Manual*, 288 (1987) 15th Ed..

To provide an effective and yet non-toxic antiviral drug which would affect the reproduction of HIV would thus be of extreme importance and a life saving measure for many thousands of AIDS victims.

Herpes simplex virus type-1 and 2 similarly are wide spread infections. They may occur in AIDS patients as one of the opportunistic infections. Type-1 HSV strain (HSV-1) commonly causes herpes labialis located on a lip, and keratitis, an inflammation of the cornea. Type-2 HSV is usually located on or around the genital area and is generally transmitted primarily by direct contact with herpetic sore or lesions. HSV-2 has been related to the development of uterine cancer.

Herpes simplex virus is very infectious and is rapidly and easily transferable by contact. There is no specific therapy to this extremely painful viral infection. Current treatment of HSV infections is primarily by systemic administration of above mentioned antiviral drugs which treatment is accompanied by undesirable adverse reactions as those described previously.

The antiviral agents used for HSV treatment are not selective inhibitors of HSV replication but affect also the replication of normal cells. Therefore, when used in doses large enough to seek and destroy all the active herpes viruses dormant in the sensory ganglia, these compounds may also be highly disruptive to the normal DNA in the host cells in which the virus multiplies. This is a very undesirable effect since the replication of normal cells is also affected.

Thus, it would be advantageous to have available non-toxic treatment of HSV infections.

Cytomegalovirus (CMV), a dangerous co-infection of HIV, is a subgroup of highly infectious viruses having the propensity for remaining latent in man. CMVs are very common among the adult population and as many as 90% of adults have been exposed to and experienced CMV infections. CMVs are normally present in body fluids such as blood, lymph, saliva, urine, feces, milk, etc. CMV infections may cause spontaneous abortion, stillbirth, postnatal death from hemorrhage, anemia, severe hepatic or CNS damage. Particularly dangerous are CMV infections afflicting AIDS patients, where CMV may cause pulmonary, gastrointestinal or renal complications. There is no specific therapy for CMVs. Contrary to the HSV, CMV is resistant to acyclovir, and to other known antiviral drugs.

Thus, it would be extremely advantageous to have available a drug which would effectively inhibit CMV infections.

The existing chemotherapeutical treatment of the most neoplastic growth and of viral infections is thus mostly limited to very toxic agents and antivirals.

Cellular and molecular events leading to malignant transformation and potential viral involvement in it are poorly understood. However, genotypically, a given cancer is believed to arise from a clone of transformed cells.

Retroviruses contain an enzyme called reverse transcriptase that can convert viral RNA in the cytoplasm into DNA, which may replicate from extrachromosomal sites or move into the cell nucleus where it becomes part of the host cell DNA. These integrated viral genes are duplicated with normal cellular genes, and all progeny of the originally infected cells will contain the viral genes. Expression of the viral genes for some retroviruses may be oncogenic, converting the cell into a cancer, or may have other pathologic effects which may alter normal cell function or produce cell death.

It is therefore a primary object of this invention to provide non-toxic, highly effective antineoplastic and antiviral drugs. 5-iodo-6-amino-1,2-benzopyrones (5-I-6-ABP) and their analogs demonstrate these desired properties.

These drugs have been now found to be agents of remarkably low toxicity, yet highly effective inhibitors of tumorigenic and viral replication in cell cultures and in human blood. Their therapeutic spectrum appears to be particularly useful for suppression and inhibition of cancer growth and for treatment of the most dangerous viral infections, such as AIDS and herpetic infections.

5-iodo-6-aminobenzopyrones have not been hitherto known or described. The only remotely related compounds found in the literature are 6-amino-benzopyrone (6-ABP) described in *J. Pharmo Soc. Jap.*, 498:615 (1923) and 3-amino-6-iodo-8-methoxy-1,2-benzopyrone, described in *J. Ind. Chem. Soc.*, 48:375 (1971). However, only scarce medicinal use for the first substance has been reported, although the testing was done for its sedative and hypnotic effects (*J. Pharm. Soc. Japan*, 73:351 (1953) and *Ibid*, 74:271 (1954), hypothermal action *Yakugaku Zasshi*, 78:491 (1958), and antipyretic, hypnotic, hypotensive and adrenolytic action was reported, *Ibid*, 83:1124 (1963). No significant action for any of those uses was found. No medical use was reported for the second compound.

The precursor molecule, 1,2-benzopyrone (coumarin), was shown to be an inhibitory ligand of adenosinediphosphoribose transferase (ADPRT), a DNA-binding nuclear protein present in neoplastic cells (*Proc. Nat. Acad. Sci. (USA)*, 84:1107 (1987)).

Recently, 6-ABP was shown to specifically bind to ADPRT at the same site that also binds catalytically effective DNA termini. It is evident that both 6-ADP and DNA compete for the same site on ADPRT. These results were disclosed in *FEBS Lett.*, 212:73 (1987), where the biological role of ADPRT was studied extensively with the aid of synthetic ligands of ADPRT and shown to inhibit DNA proliferation, particularly in tumorigenic cells. Potential antiviral effects of these ligands on viral replication was now studied and found and is the subject of the copending invention entitled "6-Amino-1-2-Benzopyrones useful for Treatment of Viral Diseases," Ser. No. 585,231, filed on Sep. 21, 1990 which is hereby incorporated by reference.

The primary objective of this invention is the discovery that novel 5-iodo-6-aminobenzopyrones (5-I-6-ABP), are specific, selective, potent and non-toxic antitumorigenic and antiviral agents. The testing of these compounds on various cancer cells and virally infected cultures, including HIV, showed that 5-I-6-ABPs are particularly useful for inhibition and suppression of cancer cell growth, and on HIV, HSV and CMV replication.

SUMMARY

One aspect of the current invention concerns novel cytostatic antitumorigenic and antiviral compounds of the formula

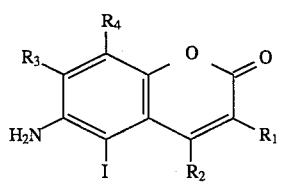

wherein $R_1$, $R_2$, $R_3$, or $R_4$ are each independently selected from hydrogen, hydroxy, amino, alkyl, alkoxy, cycloalkyl, halo or phenyl, optionally substituted with alkyl, alkoxy, hydroxy or halo, or a pharmaceutically acceptable salt thereof.

Another aspect of the current invention relates to novel cytostatic and antiviral agents having the formula

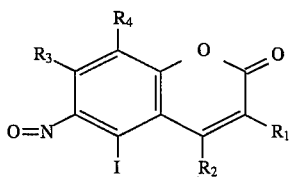

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or a pharmaceutically acceptable salt thereof.

Still another aspect of the current invention concerns a method for treatment of viral infections in a mammal comprising administering to a mammal a therapeutically effective amount of a compound of the formula

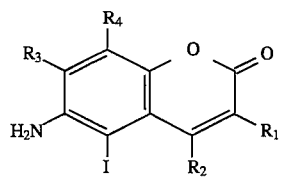

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or a pharmaceutically acceptable salt thereof.

Still yet another aspect of the current invention concerns a method for inhibiting or suppressing tumorigenic growth in a mammal comprising administering to a mammal a therapeutically effective amount of a compound of the formula

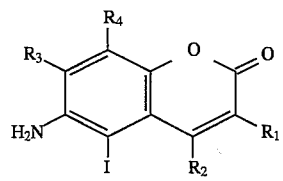

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or a pharmaceutically acceptable salt thereof.

Still another aspect of the current invention concerns a method for treatment of viral infections in a mammal by administering a therapeutically effective amount of a compound of the formula

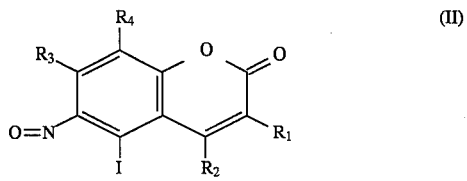

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or a pharmaceutically acceptable salt thereof.

Still another aspect of the current invention concerns a method for inhibiting or suppressing tumorigenic growth in a mammal comprising administering to the mammal a therapeutically effective amount of a compound of the formula

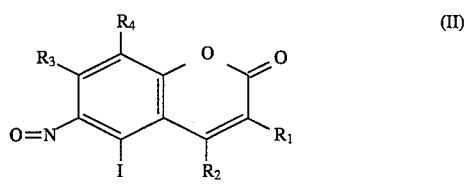

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or a pharmaceutically acceptable salt thereof.

Still yet another aspect of this invention is the method of preparation of the compound of formula

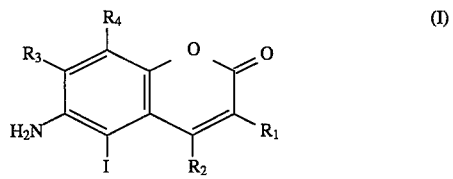

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or pharmaceutically acceptable salt thereof.

The final aspect of this invention is the method of preparation of the compound of formula

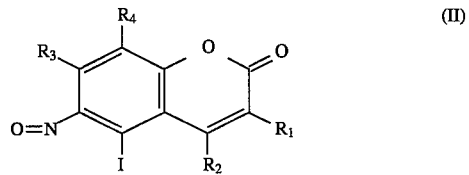

wherein $R_1$, $R_2$, $R_3$, or $R_4$ are each independently selected from hydrogen, hydroxy, amino, alkyl, alkoxy, cycloalkyl, halo or phenyl optionally substituted with alkyl, alkoxy, hydroxy or halo, or pharmaceutically acceptable salt thereof.

DETAILED DESCRIPTION OF THE INVENTION

Definitions

Figure 1A:
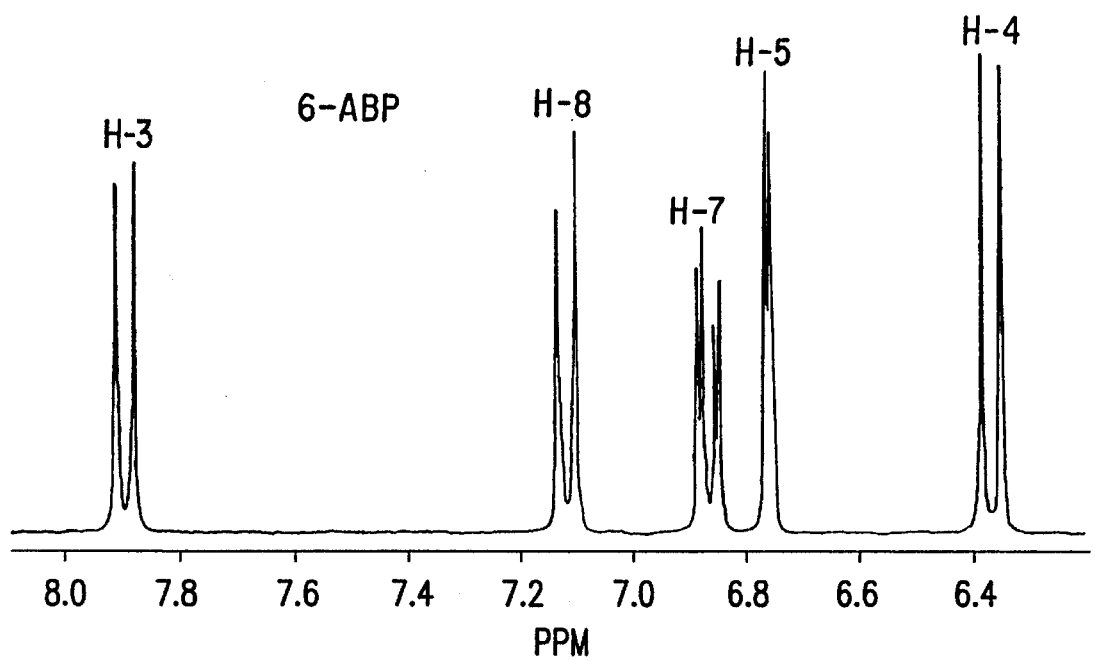
FIG. 1 shows the 'H NMR spectra of 5-I-6-ABP and its precursor, 6-ABP.

As used herein:

"Viral diseases" mean viral infections caused by retrovirus and lentivirus such as HIV-1, HIV-2, animal viruses, neurological sheep viruses, HSV-1, HSV-2, herpes zoster, CMV, Epstein Barr virus and other viruses belonging to the same class.

5-iodo-6-amino-1,2-benzopyrone or "5-I-6-ABP" refers to compounds of formula (I) substituted or unsubstituted on $R_1$, $R_2$, $R_3$, or $R_4$ corresponding to coumarin carbons 3, 4, 7 and 8, respectively, with hydrogen, hydroxy, amino, alkyl, alkoxy, cycloalkyl, halo, or phenyl optionally substituted with alkyl, alkoxy, hydroxy or halo.

"5-iodo-6-nitroso-1,2-benzopyrone" or "5-I-6-NOBP" formula (II) refers to a metabolite of 5-iodo-6-ABP which is unsubstituted or substituted on $R_1$, $R_2$, $R_3$ or $R_4$ corresponding to coumarin carbons 3, 4, 7 and 8, respectively with hydrogen, hydroxy, amino, alkyl, alkoxy, halo, cycloalkyl or phenyl optionally substituted with alkyl, alkoxy, halo or hydroxy.

"Pharmaceutically acceptable acid addition salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"ADPRT" refers to adenosinediphosphoribose transferase also known as poly (ADP-ribose)polymerase, (EC 2.4.99), a specific DNA-binding nuclear protein of eucaryotes that catalyzes the polymerization of ADP-ribose. The enzymatic process is dependent on DNA. The ADPRT enzyme is modified by 6-amino-1,2-benzopyrone in the manner described below.

"Alkyl" refers to saturated or unsaturated branched or straight chain hydrocarbon radical. Typical alkyl groups include methyl, ethyl, propyl, isopropyl, butyl, isobutyl, tertiary butyl, pentyl, hexyl and the like.

"Alkoxy" refers to the radical -0-alkyl. Typical alkoxy radicals are methoxy, ethoxy, propoxy, butoxy and pentoxy and the like.

"Cycloalkyl" refers to a saturated monocyclic hydrocarbon radical containing 3–8 carbon atoms such as cyclopropyl, cyclobutyl, cyclopentyl, cyclohexyl, cycloheptyl and cyclooctyl.

"Substituted phenyl" refers to all possible isomeric phenyl radicals mono or disubstituted with a substituent selected from the group consisting of alkyl, alkoxy, hydroxy or halo.

"Halo" refers to chloro, fluoro, bromo or iodo.

Preparation Procedures

General reaction for preparation of 5-I-6-ABPs and its metabolites 5-I-6-NOBPs, wherein $R_1$, $R_2$, $R_3$, and $R_4$ are hydrogen, hydroxy, amino, alkyl, alkoxy, cycloalkyl, halo or phenyl optionally substituted with alkyl, alkoxy, hydroxy, or halo is shown in Reaction Scheme 1.

Reaction Scheme 1

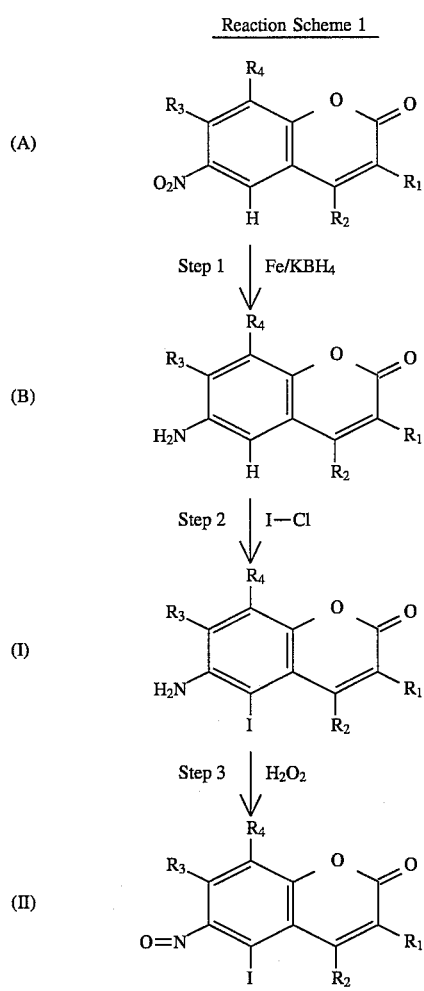

The Reaction Scheme 1 illustrates schematically the steps involved in the synthesis of 5-I-6-ABP and its metabolite 5-I-6-NOBP.

Typically, the starting compound (A) 6-nitro-1,2-benzopyrone is reduced by Step 1 to compound (B) 6-ABP, which is iodinated by Step 2 on the fifth carbon to obtain compound (I) 5-I-6-ABP which is readily oxidized by Step 3 to compound (II) 5-I-6-NOBP.

I. Preparation of 5-Iodo-6-Amino-1,2-Benzopyrones

5-Iodo-6-aminobenzopyrones of this invention are compounds having a general formula

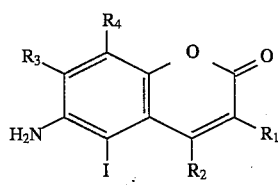

wherein $R_1$, $R_2$, $R_3$, and $R_4$ are independently chosen from hydrogen, hydroxy, amino, alkyl, alkoxy, cycloalkyl, halo or phenyl which may be optionally substituted with alkyl, alkoxy, hydroxy, or halo.

These compounds are novel. No examples have been previously described of this group of compounds in the literature.

The synthesis of the 5-I-6-ABP precursor 6-ABP compound (B) is by the spontaneous reduction of 6-nitrocoumarin compound (A), obtained from Pfaltz & Bauer, by iron powder in acetic acid followed by filtration, rotary evaporation of acetic acid, extraction into ether and crystallization from ethanol according to the method employed in *FEBS Letters,* 212:73 (1987) or by reduction of (A) by potassium borohydride using a palladium-on-carbon catalyst suspended in aqueous methanol, followed by filtration, removal of solvent, and crystallization (*J. Heterocyclic Chem.,* 23:87 (1986)). A detailed synthesis is described in Example 2.

Unsubstituted 5-iodo-6-amino-1,2-benzopyrones are generally prepared by iodination of 6-amino-1,2-benzopyrone, either as the free base or hydrochloride salt, by reaction with 1–2 equivalents of iodine reagent, such as iodine monochloride, in warm alcohol such as methanol, ethanol, propanol and other alcohols, or glacial weak acid such as acetic acid, preferably ethanol, for 5–6 minutes, preferably 10–15 minutes. In alternative, these compounds are prepared by reaction of 6-ABP with a combination of iodine and iodic acid in warm alcohol for 10 minutes to 6 hours, preferably 1–2 hours, or with iodine dissolved in a base, such as sodium hydroxide, potassium hydroxide or preferably ammonium hydroxide for 10 minutes to 6 hours, preferably 1–2 hours, at a temperature from 15° C.–40° C., preferably at room temperature. After reaction is complete, water and a convenient reducing agent, such as bisulfite, thiosulfate or other suitable reducing agent is added to destroy any unreacted iodine reagent. The iodinated product is then either precipitated by addition of excess water or extracted into a suitable organic solvent such as ethyl acetate, butyl acetate, chloroform and such others. After removal of solvent, the crude iodo-compound (I) is recrystallized from alcohol. A detailed procedure using such direct iodination of 6-ABP (B) to the 5-I-6-ABP compound is described in Example 1.

Alternatively, the 5-iodo-6-amino-1,2-benzopyrones are prepared by way of the general Perkin synthesis of 1,2-benzopyrones (coumarins), in which the suitably substituted 2-hydroxy benzaldehydes, such as for example 5-nitro-6-iodo-2-hydroxy-benzaldehyde, are condensed with glycine in the presence of anhydrous sodium acetate and acetic anhydride as described in *J. Ind. Chem. Soc.,* 49:707 (1972) to give 3-amino-5-iodo-6-nitro-1,2-benzopyrone, followed by reduction of the nitro group with aqueous sodium dithionate, to give 3-amino 5-iodo-6-amino-1,2-benzopyrone (I). This reaction could be preferable for large scale process of preparation of these compounds.

The 5-I-6-ABP compound (I) having no substitution on any of the $R_1$, $R_2$, $R_3$ or $R_4$ has been prepared and its NMR spectra compared to those of its precursor 6-ABP (B). The results are illustrated in FIG. 1.

Figure 1B:
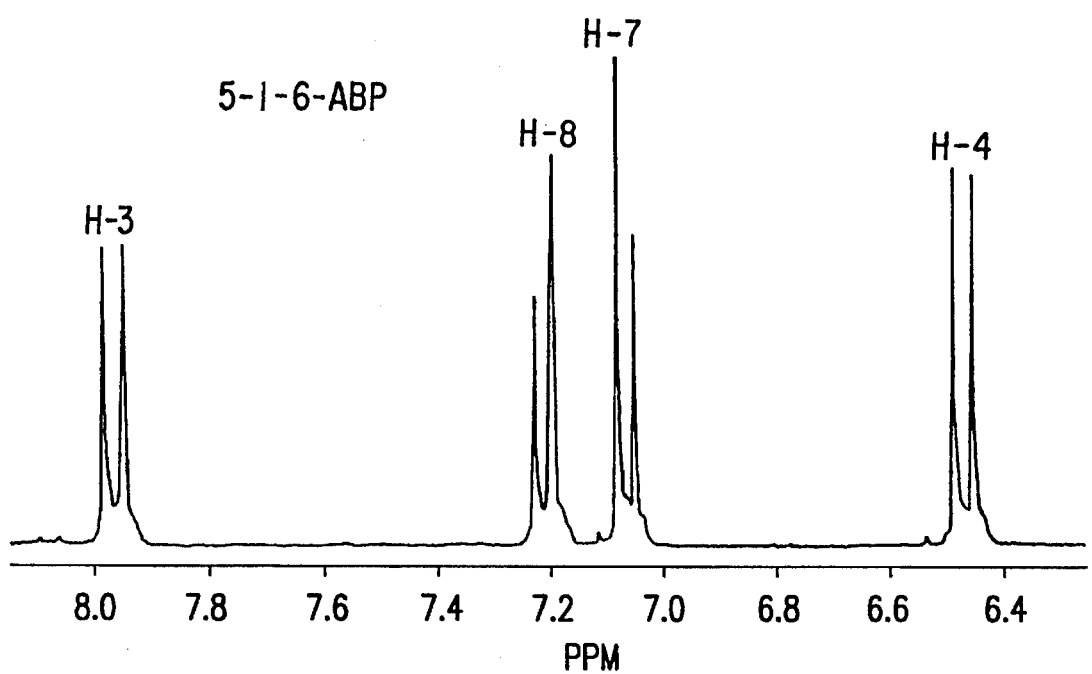

FIG. 1 specifically shows the comparison of the $^1$H NMR spectra of 5-I-6-ABP (I) and its synthetic precursor 6-ABP (B), showing nonexchangeable protons only. Proton assignments are indicated. All proton signals are doublets due to splitting by neighboring protons. In 6-ABP, H-7 is a doublet of doublets, as it is split by its close-range neighbor H-8 and additionally finely split by H-5 which is long-range (meta) to it, while reciprocally, H-5 is finely split by H-7. When 6-ABP was iodinated, the signal for H-5 disappeared and the fine splitting of H-7 likewise disappeared. In addition, some shifting of signals in the downfield direction occurred. Spectra were measured in DMSO solvent, and chemical shifts (ppm) are relative to TMS. Exact chemical shift data for 5-I-6-ABP are reported in the Example 1.

The substituted compounds are prepared generally in the same or similar way as described for unsubstituted compounds above, using the appropriately substituted 6-nitrocompound (A), either commercially available, or obtained or prepared as described in the Examples 3–10. Compounds for which no substituted precursors are available are synthesized by reactions available in the art as described below.

Alkyl derivatives of 5-I-6-ABP are typically prepared from alkylated 1,2-benzopyrones commercially available or prepared as described in the available chemical literature. Typically, for example, 7-methyl-1,2-benzopyrone, commercially available from Aldrich, and synthetic 3-methyl-1,2-benzopyrone or 4-methyl-1,2-benzopyrone prepared according *Synthesis,* 599 (1975) or 464 (1977), are respectively nitrated using nitric acid in glacial acetic acid according to *Indian J. Chem.,* 7:49 (1969), or similar mild nitration conditions, giving predominantly nitration in the 6-position, as found in *Egypt. J. Chem.,* 20:453 (1977). 6-nitro-1,2-benzopyrones are reduced to the 6-amino-derivatives using potasssium borohydride with Pd(C) catalyst in aqueous methanol employing the method described in *J. Heterocylic Chem.,* 23:87 (1986), or some other suitable reduction conditions. The reduction is followed by iodination using 1–2 equivalents of iodine monochloride (*J. Org. Chem.,* 23:1731 (1958)), wherein the 6-amino group directs monoiodination to the 5-position. Other alkylated compounds are prepared in the same or similar way.

Cycloalkyl derivatives of 5-I-6-ABP are prepared by using the cyclohexyl group to substitute for the alkyl group, as for example for the methyl group in the synthesis of 4-methyl-1,2-benzopyrone according to *Synthesis,* 464 (1977). The resulting cycloalkyl, here 4-cyclohexyl-1,2-benzopyrone is then nitrated in the 6-position using mild acid, preferably nitric acid in glacial acetic acid, and reduced to the corresponding 6-amino compound by means of sodium borohydride with Pd(C) catalyst in aqueous methanol or by any other suitable reduction procedure. The compound is then iodinated in the 5-position using one equivalent of iodine monochloride in warm alcohol, such as methanol, ethanol, propanol, butanol, etc. Other cycloalkyls are prepared in the same or similar way.

Phenyl or substituted phenyl derivatives of 5-I-6-ABP are prepared by using the method described in *Kogyo Kagaku Zasshi,* 71:1010 (1968) and in *Chem. Abstr.,* 70:30023 (1969). For example, the p-tolyl group is used to substitute for the phenyl group in the synthesis of 6-amino-3-phenyl-1,2-benzopyrone to give 6-amino-3-p-tolyl-1,2 benzopyrone. This compound is then iodinated by using one equivalent of iodine monochloride in alcohol. The 6-amino group activates and directs iodination at the 5-position. Other aryl derivatives are prepared in the same or similar fashion. To attach the phenyl group to other positions, the methods available in the art are used for such purposes.

Hydroxy derivatives of 6-ABP are typically prepared from commercially available synthetic precursors such as 4-hydroxy-1,2-benzopyrone (Aldrich) by nitration under mild conditions such as nitric acid in glacial acetic acid according to *Indian J. Chem.*, 7:49 (1969) giving the corresponding 6-nitro-derivatives which are then reduced to the amino compounds by means of sodium or potassium borohydride with Pd (C) catalyst in aqueous alcohol or by other reduction procedures. Other hydroxylated 5-I-6-ABP compounds are prepared in the same or similar fashion.

Alkoxy derivatives are typically easily prepared from above described hydroxy derivatives. As an example, the 6-nitro-derivative of the 4-hydroxy-1,2-benzopyrone described above is treated with dimethyl sulfate according to *Synthesis*, 144 (1978) to convert the hydroxy group to a methoxy group, and then the resulting compound is reduced to 4-methoxy-6-amino-1,2-benzopyrone using sodium or potassium borohydride with Pd(C) catalyst in aqueous alcohol, preferably methanol. The compound is then iodinated with equivalent amount of iodine monochloride in alcohol to yield the 5-iodo-derivative. Other alkoxy compounds are prepared in the same or similar fashion.

Amino derivatives of 5-I-6-ABP are prepared, for example, by using precursors having the additional amino group(s) substituents on $R_1$–$R_4$, such as for example, synthetic 3-amino-6-nitro-1,2-benzopyrone prepared according to *Arch. Pharm.*, 296:365 (1963). The amino-nitro compound is then reduced to 3,6-diamino-1,2-benzopyrone using sodium or potasssium borohydride with Pd(C) catalyst in aqueous alcohol, preferably methanol or by other suitable reduction procedure. The compound is then iodinated with one equivalent of iodine monochloride in alcohol, wherein the 6-amino group directs iodination to the 5-position. The other di-or tri-aminoderivatives are prepared in the same or similar way.

Halo derivatives of 5-I-6-ABP are prepared either by starting with a desired synthetic halo-substituted 1,2-benzopyrone which is then successively nitrated in the 6-position, reduced to the amino-compound and iodinated in the 5-position, or by subjecting the 5-I-6-ABP to direct halogenation using bromine or iodine. Thus, typically, 3-fluoro-1,2-benzopyrone described in *J. Chem. Soc.*, 4033 (1961), or 3-chloro- and 3-bromo-1,2-benzopyrone described in *J. Org. Chem. USSR* (Eng.) 7:386 (1971) are nitrated with nitric acid in glacial acetic acid to give the respective 6-nitro-derivatives, which are then reduced with aqueous sodium dithionate or sodium or potassium borohydride/Pd(C) to the corresponding 6-amino-derivatives, which in turn are iodinated with one equivalent of iodine monochloride in alcohol to give the respective 3-halo-5-iodo-6-amino-1,2-benzopyrones. As an example of direct halogenation, using two equivalents of the reagent comprised of iodine in ammonium hydroxide (*J. Org. Chem.*, 23:1731 (1958)), 6-amino-1,2-benzopyrone is iodinated to 5,7-diiodo-6-amino-1,2-benzopyrone.

The most preferred compound of the current invention is 5-iodo-6-amino-1,2-benzopyrone (5-I-6-ABP), compound I. However, the iodo substitution in 5-position and amino substitution in 6-position in combination with hydrophilic and hydrophobic substitution $R_1$, $R_2$, $R_3$ and $R_4$ in 1,2-benzopyrone (coumarin) positions 3, 4, 7 and 8, confers similar or better cytostatic and antiviral biological activity on these variants of 5-I-6-ABP, and are intended to be within the scope of this invention.

II. Preparation of 5-Iodo-6-Nitroso-1,2-Benzopyrones

Compound (I) of the current invention is readily converted or metabolized to its nitroso compound (II) forming thus 5-iodo-6-nitroso-1-2-benzopyrone (5-I-6-NOBP). Compound 5-I-6-NOBP is also a preferred compound of this invention. Similarly to 5-I-6-ABP (I), 5-I-6-NOBP (II) is also useful for inhibition and suppression of neoplastic growth and viral replication.

Typically, the nitroso-compounds are prepared either in aqueous solutions or in aqueous alcoholic solutions, wherein the parent 5-iodo-6-amino-compound (I) is dissolved or in suspension, and the solution preferably contains an equivalent of mineral acid such as for example hydrochloric acid, sulfuric acid, phosphoric acid, boric acid and such others, preferably hydrochloric acid, and tungstic acid or its salts, or any other oxyacid capable of forming peroxy groups, and an excess of hydrogen peroxide. After completion of the reaction, preferably at room temperature or below, the nitroso-product is extracted in an organic solvent such as ethyl acetate, or chloroform and purified by chromatography on silica gel using as eluting solvent ethyl acetate, chloroform, hexane, or mixtures thereof.

Alternatively, the oxidation is carried out in nonpolar solvents, such as chloroform, dichloromethane or other wherein the parent amino compound (I) is dissolved and combined with 1–2 equivalents of an organic peroxyacid, such as peroxybenzoic acid, metachloroperoxybenzoic acid, or peroxyacetic acid, administered preferably at temperatures from 0° C. to 40° C., preferably at room temperature or below. After completion of the reaction, the mixture is concentrated by evaporation of solvent and the nitroso-product (II) is isolated by chromatography on silica gel using an eluting solvent such as mentioned above.

UTILITY 5-iodo-6-amino-1,2-benzopyrones (I) and their nitroso metabolites (II) are potent, specific and non-toxic antineoplastic and antiviral drugs which selectively inhibit growth of tumor cells and viral reproduction, particularly in viruses such as human immunodeficiency viruses, HIV-1, HIV-2, herpetic viruses, HSV-1, HSV-2, herpes zoster or, Epstein Barr virus (EBV), animal viruses, neurological sheep viruses, and CMV. Consequently, these drugs are useful for prevention and treatment of tumorous and viral diseases. These compounds are particularly effective inhibitors of tumor growth in immunosuppressed patients with AIDS where they affect not only the tumor growth such as Kaposi's sarcoma but also inhibit human immunodeficiency virus, and the development of opportunistic infection due to herpes simplex virus and cytomegalovirus and opportunistic neoplastic growths such as Kaposi sarcoma, nonHodgkin lymphoma and primary lymphoma. In case of viruses, these compounds are thus particularly useful for treatment of AIDS, herpetic lesions and cytomegalovirus infection. Moreover, these compounds have very low, if any, toxicity.

5-I-6-ABP and/or its metabolite 5-I-6-NOBP have been now found to be a potent inhibitor of ADPRT. Their biological action spectrum is nearly the same as that of 6-ABP, except that their potency is about 10–50 times greater. Such potency is particularly well documented in the case of 5-I-6-ABP against malignant cell proliferation in cell cultures. 5-I-6-ABP is also highly effective against HIV. This effectivity is 10–20 times higher than 6-ABP.

While the much tighter binding of 5-I-6-ABP to ADPRT seems to account for the greater biological action of this molecule as compared to 6-ABP, the basic molecular mechanism of action on a chemical level is probably the same. The 6-amino group of 5-I-6-ABP is rapidly oxidized intracellularly to 5-I-6-NOBP which, by binding to the $Zn^{2+}$ finger domain of ADPRT, destabilizes the tightly chelated $Zn^{2+}$ by the oxidation of the thiol groups in the $Zn^{2+}$ finger polypeptide, thus ejecting $Zn^{2+}$. In this way, 5-I-6-ABP effectively inactivates the ADPR-forming activity of this protein and converts it to a DNA binding protein that reacts with "internal domains" of certain double stranded DNA (*Biochemistry*, 28:5670 (1989); *Biochem. Biophys. Res. Commune*, 167:842 (1990)). These DNA domains include abnormally replicating DNA structures in tumorigenic or proliferative cells and in viral DNAs, probably at the integration sites.

Antiviral and antitumorigenic activity of 6-ABP (B) has been previously described in the pending U.S. applications Ser. No. 333,844 filed Apr. 4, 1989, Ser. No. 412,783 filed on Sep. 26, 1989 and Ser. No. 585,231 filed on Sep. 21, 1990, all now abandoned incorporated herein by reference.

Antiviral Activity of 5-I-6-ABP

The current iodo-compounds of formula (I), in particular 5-I-6-ABP are about 10 times more potent (on a concentration basis) than the non-iodinated 6-ABP. Where the $I_{50}$ of 6-ABP is 125 µM and $K_i$ is 47 µM; $I_{50}$ of 5-I-6-ABP is 19 µM and $K_i$ is 2 µM.

Figure 2:
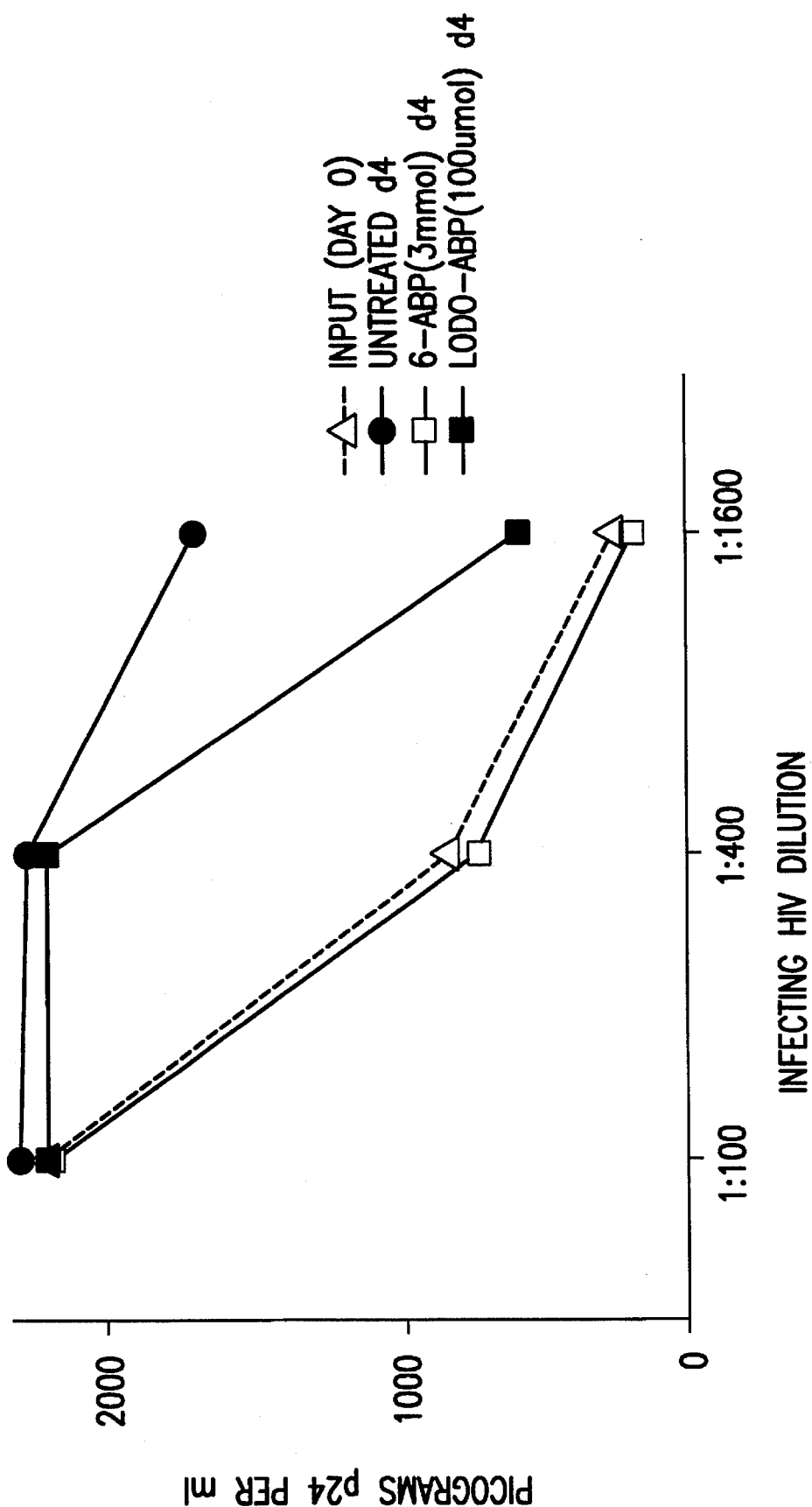
FIG. 2 shows the HIV (p24) inhibition by 5-I-6-ABP compared to 6-ABP in AA-2 cells.

The anti-HIV activity of 5-I-6-ABP, compared with 6-ABP is illustrated in FIG. 2, where virulent HIV propagation is assayed in AA-2 cell cultures.

FIG. 2 shows the effect of extracellularly applied 5-I-6-ABP, and 6-ABP, compared to untreated cultures, on the time course of viral propagation in AA-2 cells in culture. The effect of 3 mM 6-ABP was compared with the effect of 0.1 mM 5-I-6-ABP on HIV replication at 4 days using the conventional analysis of p24 formation by automated ELISA tests. As seen from FIG. 2, at day 4, a 30 times lower amount (0.1 mM) of 5-I-6-ABP had almost equivalent suppressing effect on p24 generation at 1:1600 HIV dilution as had 3 mM of 6-ABP. This clearly shows that the 5-I-6-ABP is a much more potent inhibitor of the HIV proliferation.

Figure 3:
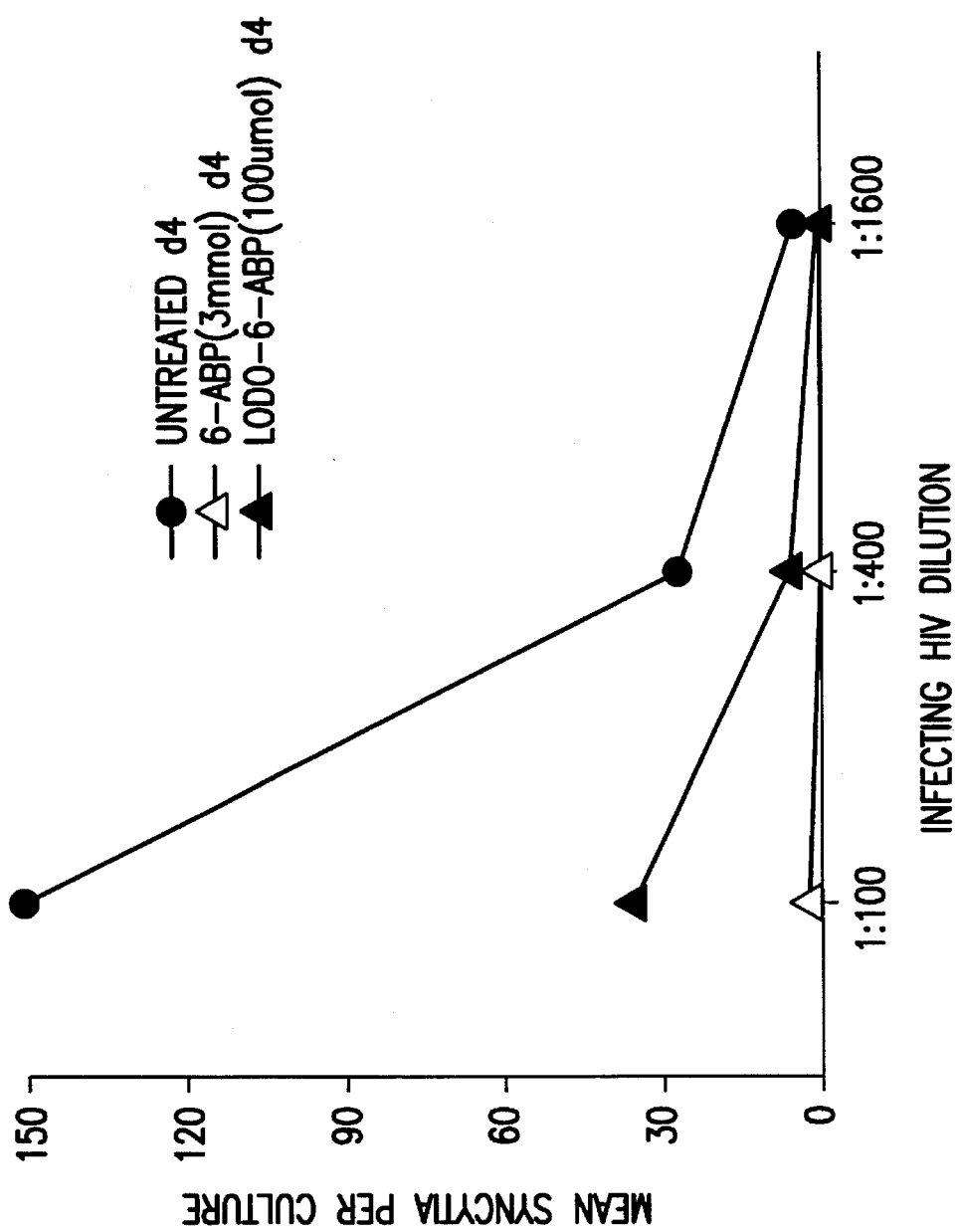
FIG. 3 shows the inhibitory effect on syncythia formation in MT2 cells of 5-I-6-ABP compared to 6-ABP.

In FIG. 3 which shows the inhibition of syncytia formation in MT-2 cells by both 5-I-6-ABP and 6-ABP, the effectivity of both compounds on the syncytia formation is even more pronounced. At 1:1600 HIV dilution, the inhibition is complete for both drugs. In 1:400 dilution, the 30 times lower amount of 5-I-6-ABP (0.1 mM) is only slightly less inhibitory than 3 mM 6-ABP. This is also seen in 1:100 HIV dilution. All these observations are done on day 4.

Figure 4:
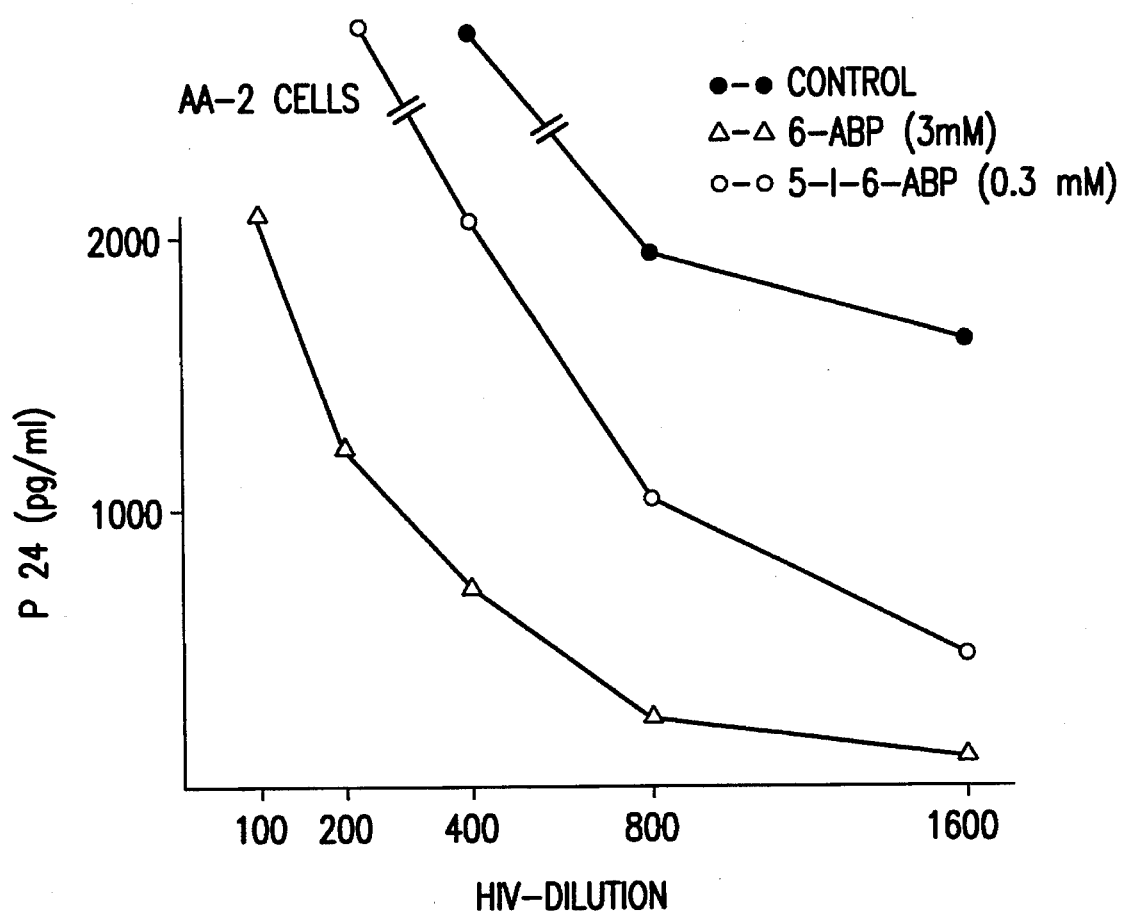
FIG. 4 shows the anti-HIV activity of 5-I-6-ABP compared to 6-ABP measured by p24 protein formation.

FIG. 4, similarly to FIG. 2, shows p 24 protein formation as a measure of HIV replication and compares the effects of 3 mM 6-ABP with the effect of 0.3 mM 5-I-6-ABP. Here, a similar effect is seen as in FIG. 2. The amount of 6-ABP here is only 10 times higher than that of 5-I-6-ABP. Thus, ten times lesser concentration of 5-I-6-ABP is nearly as effective in all tests compared to the concentration of 6-ABP.

Figure 5:
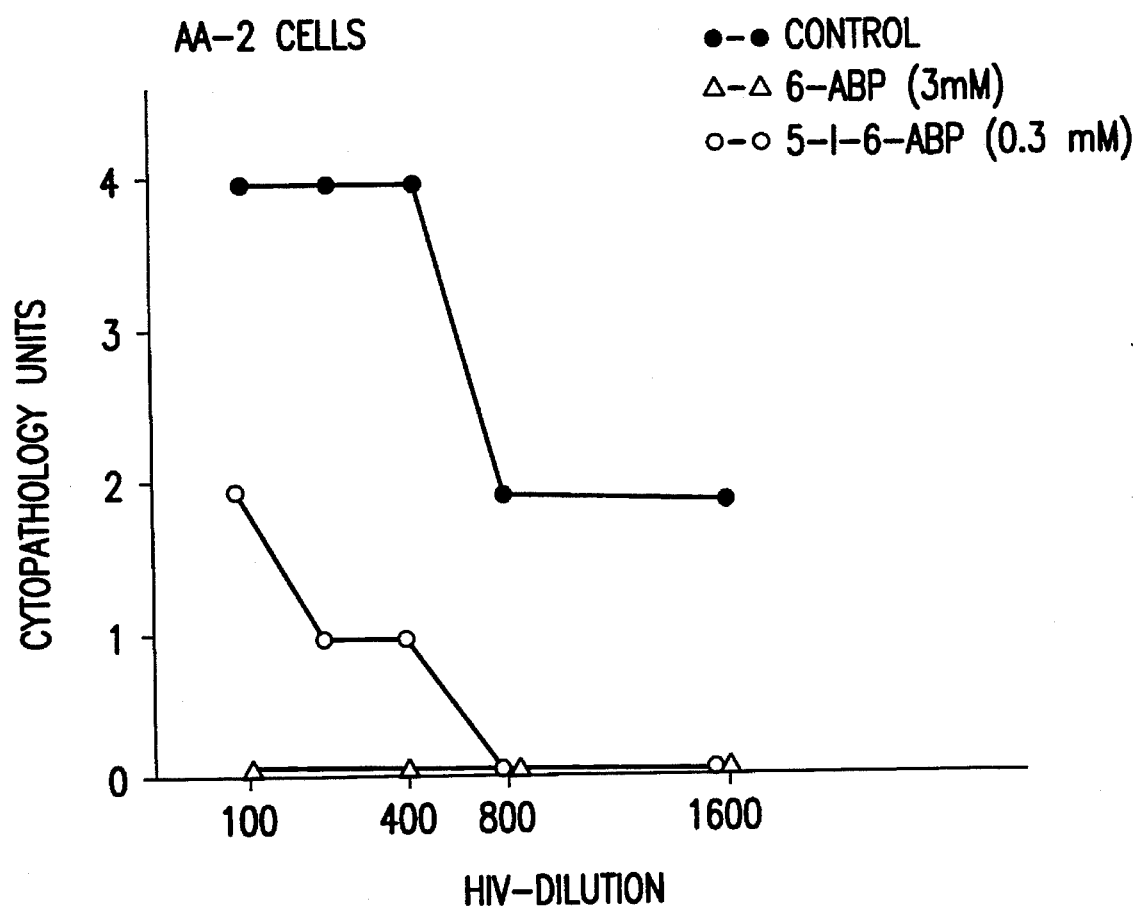
FIG. 5 shows the anti-HIV activity of 5-I-6-ABP compared to 6-ABP assayed by the cytopathogenic effect of HIV on AA-2 cells.
Figure 6:
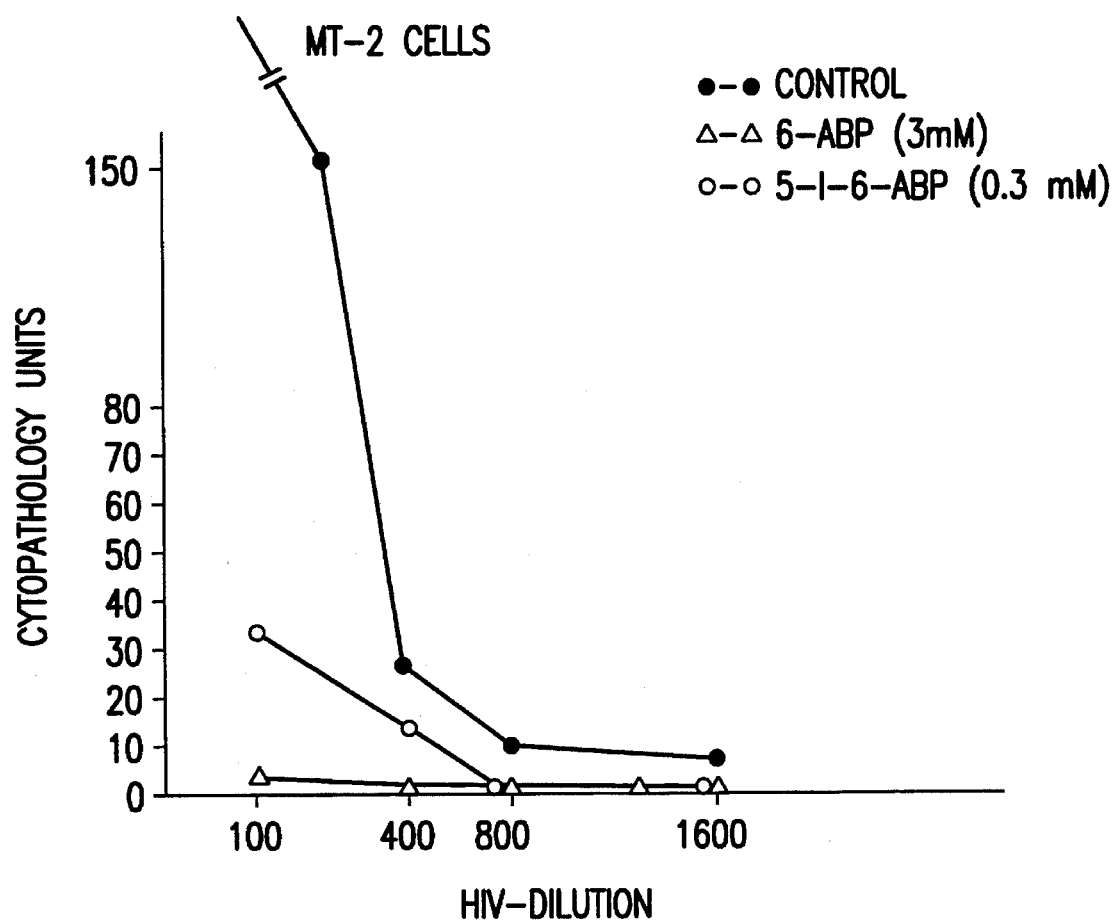
FIG. 6 shows the anti-HIV activity of 5-I-6-ABP compared to 6-ABP assayed by the cytopathogenic effect of HIV on MT-2 cells.

FIGS. 5 and 6 show the same comparison of 6-ABP with 5-I-6-ABP, except that viral growth is assayed by the cytopathogenic effect of HIV on AA-2 cells (FIG. 5) and MT-2 cells (FIG. 6). Thus, ten times lower concentration of 5-I-6-ABP is nearly as effective in all tests as compared to the concentration of 6-ABP.

Therefore, 5-I-6-ABPs are useful for treatment of diseases where abnormally stimulated DNA synthesis occurs, such as in viral and in chronic inflammatory diseases. These drugs may be used alone or in combination with 6-ABP.

Cytostatic Effects of 5-I-6-ABP

Based on the same mode of action, 5-I-6-ABP possesses also a very potential cytostatic anti-tumorigenic activity. Such activity has been studied on cell lines and is described in detail in Example 11.

Results are shown in the Table 1 where DNA synthesis is being assayed in 6 different cell lines. In all cases, replication of particularly tumorigenic cell types is profoundly inhibited by 5-I-6-ABP treatment. 500 µM 6-ABP has shown the same effectivity as 50 µM, 5-I-6-ABP, i.e., the tumorigenic activity of 5-I-6-ABP was at least 10 times or more higher.

Cytostatic effects of 5-I-6-ABP which do not involve cellular toxicity predestine this molecule as a drug of choice in treatment of metastatic cancers, following surgical removal of main tumor mass.

5-I-6-ABP compounds and their metabolites have been found to be potent and nontoxic pro-drugs which very specifically and effectively inhibit the tumorous cell mitosis and viral DNA replication. Both 5-I-6-ABP and 5-I-6-NOBP may inhibit the DNA replication by converting ADPRT into a DNA template inhibitor.

The mode of action of these compounds appears to be as follows. 5-I-6-ABP is a "pro-drug" which penetrates most mammalian cells to a limited degree at physiological pH 7.2–7.4. In the cell, 5-I-6-ABP undergoes rapid oxidation at the 6-amino position to 5-iodo-6-nitroso-1,2 benzopyrone (5-I-6-NOBP) which is the reactive species. 5-I-6-NOBP binds with high affinity to zinc-fingers of enzyme ADPRT and by oxidizing the SH groups of these zinc fingers to —S-S— groups thus eliminates or ejects zinc from ADPRT. Zinc ejection metabolically inactivates ADPRT and converts it to a selective DNA binding protein. It is estimated that in maximally replicating cells the number of DNA templates is approximately 25,000, whereas the number of ADPRT molecules in 160–180,000, thus in excess to bind to each template. This protein (ADPRT) then binds to the DNA templates and inhibits DNA replication. ADPRT, which possesses a specific 5-I-6-ABP site exclusively, thus becomes a very selective inhibitor of viral and tumorigenic replication.

The high reactivity of 5-I-6-ABP oxidation product 5-I-6-NOBP seems to be caused by its swift reaction with cellular glutathione ultimately reducing it back to 5-I-6-ABP. This would explain the absence of nonspecific cellular toxicity of this drug, and the presence of its high efficacy by virtue of its specific binding to its own ADPRT site. Since the 5-I-6-ABP binding site is exclusive for ADPRT, no other enzymes are activated or inhibited by 5-I-6-ABP and, consequently, the 5-I-6-ABP drug is completely nontoxic. The toxicity studies are described in Example 15.

The apparent low toxicity of 5-I-6-ABP can be further explained by the rapid metabolic reduction of the intracellularly generated 5-I-6-NOBP derivative by reduction by glutathione to the hydroxylamine and eventually to 5-I-6-nitroBP. In addition, the oxidation of 5-I-6-NOBP to 5-I-6-nitro-NBP, a reaction that occurs in the liver, converts the biochemically active molecule to the inactive nitro-product. This reduction-oxidation cycle is high in liver but much lower in target cells, such as for example lymphatic cells.

5-I-6-ABP is a specific, potent and non-toxic inhibitor of HIV, HSV and CMV. However, 5-I-6-ABP is not a specific retroviral inhibitor, since it is effective also in HSV and in other nonretroviral viruses. Its antiviral specificity is related to the drug induced inhibition of specific binding sites in DNA at integration sites by ADPRT that had been modified by $ZN^{2+}$ loss at one $ZN^{2+}$ finger site. Consequently, the growth of any viral DNA which involves ADPRT binding would be inhibited with 5-I-6-ABP.

In practice, the compounds of this invention, namely substituted or unsubstituted 5-I-6-ABP of formula (I) or 5-I-6-NOBP (II) or any of their pharmaceutically acceptable salts, will be administered in amounts which will be sufficient to inhibit the neoplastic growth or the viral expression or prevent the development of the cancerous growth or viral infection in the host cell and in the pharmaceutical form most suitable for such purposes.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical tumors or lesions, where topical administration may be preferable. In other instances, it may be necessary to administer the composition in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of active 5-I-6-ABP compound of formula (I), 5-I-6-NOBP compound (II) or the pharmaceutically acceptable salt thereof, and in addition, it may include any conventional pharmaceutical excipients and other medicinal or pharmaceutical drugs or agents, carriers, adjuvants, diluents, etc., as customary in the pharmaceutical sciences.

For solid compositions, in addition to the active 5-I-6-ABP compound of formula (I), or 5-I-6-NOBP (II), such excipients as for example, pharmaceutical grades of mannitol, lactose, starch, magnesium stearate, sodium saccharin, talcum, cellulose, glucose, sucrose, magnesium carbonate, and the like may be used. The active 5-I-6-ABP compound (I), or 5-I-6-NOBP (II) as defined above, may be also formulated as suppositories using, for example, polyalkylene glycols, for example, propylene glycol, as the carrier.

Liquid, particularly injectable compositions can, for example, be prepared by dissolving, dispersing, etc. an active compound (I) or (II) in a pharmaceutical solution such as, for example, water, saline, aqueous dextrose, glycerol, ethanol, and the like, to thereby form the injectable solution or suspension.

If desired, the pharmaceutical composition to be administered may also contain minor amounts of nontoxic auxiliary substances such as wetting or emulsifying agents, pH buffering agents, and the other substances such as for example, sodium acetate, triethanolamine oleate, etc.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of a slow-release or sustained-released systems, which assures that a constant level of dosage is maintained, according to U.S. Pat. No. 3,710,795, which is incorporated herein by reference.

Normally, 5-I-6-ABP would not be effective per os because of its rapid conversion in the liver to the 5-I-6-nitroBP. However, appropriate chemical modification of 5-I-6-ABP which could prevent such rapid metabolism in the liver is possible and is within the scope of this invention.

Any of the above pharmaceutical compositions may contain 0.1–99%, preferably 1–70% of the active 5-I-6-ABP ingredient.

Actual methods of preparing such dosage forms are known, or will be apparent to those skilled in this art, and are in detail described in *Remington's Pharmaceutical Sciences*, Mack Publishing Company, Easton, Pa., 17th Edition, 1985. The composition or formulation to be administered will, in any event, contain such quantity of the active compound(s) which will assure that a therapeutically effective amount will be delivered to a patient. The therapeutically effective amount means an amount effective to prevent development of or to alleviate the existing symptoms of the subject being treated.

The amount of active compound administered will, of course, be dependent on the subject being treated, on the subject's weight, the severity of the affliction, the manner of administration and the judgment of the prescribing physician. However, an effective dosage is in the range of 0.001 to 5000 mg/kg/day, preferably 0.01 to 1000 mg/kg/day, more preferably 0.1 to 100 mg/kg/day. Generally, the upper limit for the drug dose determination is its efficacy balanced with its possible toxicity. However, since such toxicity has not been observed in animal (rodent) experiments for the compounds of this invention, the administered dose may be as high as needed to achieve desirable therapeutical effect.

Various substituents of 5-I-6-ABP as shown in formulae, are likely to modify lipid solubility rate of cellular penetration, thus clinical dosage schedules the above biochemical mechanism is not likely to be altered on a molecular level by substituents.

5-I-6-ABP, is a reasonably soluble molecule. It can form approximately 0.4 mM solution in water at pH 7.2–7.9, which is stable for months at room temperature, and if kept in the dark it shows only trace (less than 0.10%) decomposition. Such solution would be reasonably stable for use as an intravenous infusion formulation. The parenteral route of administration seems to be the most likely effective mode of administration against cancer or HIV infections at any stage of the disease. Since 5-I-6-ABP appears to cross the blood brain barrier, it will be also useful for treatment of AIDS neurological disorders. 5-I-6-ABP is most probably also effective for treatment of AIDS related Kaposi's sarcoma of inner organs. Properly formulated, it will also effect skin disorders.

The chemotherapy may be repeated intermittently while tumors or HIV infections are or even when they are not detectable.

Moreover, due to its apparent nontoxicity, the 5-I-6-ABP therapy may be provided alone or in combination with other antiviral or other drugs, such as for example with its precursor 6-ABP (B), AZT, anti-inflammatories, antibiotics, corticosteroids, vitamins and other such drugs. There are no contraindications to use 5-I-6-ABPs with even such toxic drug as AZT or other drugs since 5-I-6-ABPs are nontoxic and their modes of action are quite different. Possible synergism between 5-I-6-ABP and other drugs is expected and predictable.

5-I-6-ABP compounds are equally useful for treatment of herpetic lesions caused by both HSV-1 and HSV-2. The drug would be preferably administered by i.v. infusion or other parenteral or systemic mode of administration. In case of sores, the drug could be also administered topically. Infection caused by CMV would be treated preferably in the same fashion as that suggested for AIDS treatment.

One primary advantage of the 5-I-6-ABP is the absence of toxicity. Since the drug is acting very specifically only on the enzyme ADPRT responsible for tumorigenic mitosis and for viral reproduction and is not acting on any other enzyme, it does not seem to have any undesirable side effects.

Substituted 5-I-6-ABPs, containing substitution on $R_1$–$R_4$ which produce more lipophilic molecules render pharmaceuticals that more readily penetrate the cell wall and may have even more higher efficiency than 5-I-6-ABP, and thus may be more effective at lower concentrations.

The following preparations and examples serve to illustrate the invention. They should not be construed as narrowing it, or limiting its scope.

METHODS AND MATERIALS

Virological Methods

Cells and Viruses

Vero (African green monkey kidney) and MRC-5 (human lung fibroblast) cells (M.A. Bioproducts, Walkersville, Md.) were grown in Eagle's minimal essential medium (MEM) with 25 mM Hepes buffer and 10% fetal bovine serum (FBS). Human epidermoid carcinoma No. 2 (HEp-2) cells were grown in medium 199 with 10% FBS. Rhesus monkey kidney (RMK) cells obtained commercially from M.A. Bioproducts, were grown in Eagle's MEM and maintained with 2% FBS. U937 human monocytic cells were grown in RPMI with 10% FBS and 1% sodium pyruvate. MT2, T cell leukemia cells originally obtained from NIH, were grown in RPMI 1640 with 10% FBS.

Herpes simplex virus (HSV) type 1 and 2 (F and G strains, respectively) were grown in HEp-2 cells and titered by plaque assay under liquid overlay as described in *Proc. Natl. Acad. Sci.*, 83:2787 (1986).

Cytomegalovirus (CMV) were original patient isolates obtained in clinical service. CMV was grown in MRC-5 cells in MEM with 10% FBS, respiratory syncitic virus in HEp-2 cells in MEM with 2% FBS, Adenovirus, Influenza and Enterovirus in RMK cells in MEM with 0.8% Bovine serum albumin (Fraction V) and 25mM Hepes buffer (influenza) or 2% FBS (Adenovirus, Enterovirus). HIV-1 was originally obtained from NIH and grown in Molt 3 cells.

Virus titers for CMV are expressed as the highest dilution that causes 50% cytopathic effect (TCID50). Virus titers for HSV-1 and HSV-2 are expressed as syncytial forming units (PFU) per ml. HIV titers are expressed as syncytial forming units (SFU per ml), assayed on MT2 cells.

EXAMPLE 1

Preparation of 5-Iodo-6-Amino-1,2-Benzopyrones

This example illustrates the preparation of 5-iodo-6-amino-1,2-benzopyrones.

Chemical Synthesis and Characterization of 5-I-6-ABP

The method employed is a modification of a procedure described in the *J. Org. Chem.*, 23:1731 (1958) using iodine monochloride to introduce iodine into coumarin (1,2-benzopyrone) compounds.

To a stirred solution of 6-amino-1,2-benzopyrone hydrochloride (4.95 g., 0,025 mole) in 500 ml of 95% ethanol at 60° C. was added iodine monochloride (8.12 g., 0,050 mole), and after 10 minutes at 60° C. TLC analysis indicated that all of the 6-ABP had reacted. The mixture was then cooled and transferred to a 4-liter flask to which was added 700 ml of ethyl acetate, 500 ml of water and 25 ml of aqueous 2M sodium bisulfite (pH 7.4). The mixture was swirled vigorously to allow bisulfite to destroy excess iodine reagent, which otherwise contaminates the product. After addition of more water (500 ml), giving rise to a separation of phases, the upper layer (ethyl acetate) was isolated from the lower (aqueous), and in a separatory funnel the former was washed three times with 200-ml volumes of water and combined with two 300-ml ethyl acetate extracts of the aqueous layer. After drying over sodium sulfate the solution was stripped of solvent by rotary evaporation, yielding 6.40 g. of dry, brown-colored crude product which was then dissolved in 200 ml of boiling hot absolute ethanol, filtered to removed a small amount of sediment, and condensed to a volume of 125 ml. Upon cooling, dark brown product crystals deposited (4.09 g., m.p. 159°–165° C.) which were then recrystallized from 50 ml of hot ethanol, yielding 3.72 g. (52% yield) of the pure title compound (m.p. 163°–165° C.).

The color of the compound in the solid state depends on particle size. Large crystals are a very deep brown, small crystals, a medium brown, and when pulverized, the material in all cases is orange-colored. In contrast to its precursor (6-ABP), the title compound does not form salts with common mineral acids. At 25° C., it is sparingly soluble in water (saturated at $3.7 \times 10^{-4}$ Molar), moderately soluble in ethanol (saturated at $4.7 \times 10^{-3}$ Molar), and very soluble in DMSO (saturated at 1.9 Molar), and the compound is stable in all of these solvents. Additionally, it is noted that the compound is stable with respect to boiling water.

Elemental Analysis for $C_9H_6INO_2$: Calculated: C, 37.65; H, 2.11; I 44.23; N, 4.88. Found: C, 38.01; H, 1.93; I, 43.96; N, 4.53.

Mass Spectrum: m/z (relative intensity): 287 (M+, 100), 259 (3.29) 191 (2.55), 160 (78.24), 143 (2.33), 132 (40.88), 104 (25.18). High-resolution data for M+ peak: calculated for $C_9H_6INO_2$, 286.9443; found, 286.9442 (deviation=−0.5 ppm).

UV Absorption Spectrum: λmax 386 nm ($\epsilon 2.88 \times 10^3$) λ max 298 nm ($\epsilon 1.11 \times 10^4$), λ max 246 nm ($\epsilon 2.01 \times 10^4$), and λ max 212 nm ($\epsilon 2.11 \times 10^4$) in absolute ethanol.

$^1$H NMR spectrum in DMSO-$d_6$ (δ (ppm) values relative to TMS): broad singlet (5.4454) due to the protons of the amino group; doublet (6.4522 and 6.4850) due to H-4 split by H-3; doublet (7.0494 and 7.0792) due to H-7 split by H-8; doublet (7.1934 and 7.2230) due to H-8 split by H-7; and doublet (7.9522 and 7.9849) due to H-3 split by H-4. Assignment of the iodine atom to position-5 in the 1,2-benzopyrone ring system is based on comparison of the $^1$H NMR spectrum of the precursor molecule (6-amino-1,2-benzopyrone) with the iodo-derivative. The former molecule displays a doublet (6.7513 and 6.7600) attributed to H-5 (split by H-7) which is absent in the iodo-derivative, while all of the other corresponding nonexchangeable proton signals are present.

$^{13}$C NMR spectrum in DMSO-$d_6$ (δ (ppm) values relative to TMS): 83,168 (C-5), 117,078 (C-3), 117,253 (C-8), 118,162 (C-7), 120.733 (C-10), 145.538 (C-9), 146.495 C-4), 147,239 (C-6), and 159,828 (C-2). The carbon atom displaying the smallest δ value (most shielded) is that which is bonded to the iodine atom (C-5), while that with largest value (least shielded) is the carbonyl carbon (C-2). Precedents for such assignments are available in *Tetrahedron*, 33:899 (1977). Substitution of the iodine atom for a hydrogen on C-5 causes a chemical shift change from 110,130 (C-5 in the precursor) to 83,168 in the title compound.

EXAMPLE 2

Preparation of 6-Amino-1,2-Benzopyrones

This example illustrates the preparation of 6-amino-1,2-benzopyrones, compound (B), precursors to 5-iodo-6-amino-benzopyrones.

Preparation of 6-amino-1,2-Benzopyrones

The method employed to prepare 6-ABP is a modification of a published procedure in *J. Heterocylic Chem.*, 23:87 (1968).

In a fume hood, to 0.50 g of 10% palladium catalyst on activated carbon suspended in 30 ml of water in a 125 ml flask a solution of potassium borohydride (2.70 g., 0,050 mole) in 35 ml of water was slowly added. The combined mixture was then transferred to a 2-liter flask equipped with a magnetic stirrer and a solution of commercial 6-nitro-1,2-benzopyrone compound (A) (3.82 g., 0.020 mole) in 1000 ml of methanol was gradually added at room temperature. After addition was complete the mixture was stirred for 15 minutes more, suction filtered through Celite on a Buchner funnel to remove the catalyst and stripped of methanol by rotary evaporation. The residue was collected by suspending it in cold water and pouring onto a Buchner funnel. After drying, the material 6-ABP (B) was recrystallized from ethanol to give 2.18 g (68% yield) of the yellow product, m.p. 166°–169° C. Mass spectrum: 161 (M+), 133, 104, 78, 52.

EXAMPLE 3

Preparation of 5-Iodo-6-nitroso-1,2-benzopyrone

This example illustrates preparation of 5-iodo-6-nitroso-1,2-benzopyrones.

To stirred solution of 0.431 g (1.50 mMol) of 5-iodo-6-amino-1,2-benzopyrone in 60 ml of 50% aqueous ethanol was successively added 0.85 ml of 2M HCl, 0,441 g (1.50 mMol) of sodium tungstate dissolved in 3.0 ml of water, and 3.6 ml of 30% aqueous hydrogen peroxide. After stirring for 2 hours at room temperature, TLC analysis showed that approximately 10% of the amine had reacted. At this time, an additional 0.5 ml of the peroxide reagent was added to the mixture, and stirring was continued overnight, for a total of 21 hours at room temperature, at which point TLC analysis indicated that about 90% of the amine had reacted. An additional 0.50 ml of peroxide reagent was added and the mixture was stirred for 3 hours more, and then transferred to a separatory funnel, to which was also added 50 ml of water and 200 ml of ethyl acetate. The organic products were extracted into the ethyl acetate layer, which was then separated and washed with 100 ml of distilled water. The reddish-brown ethyl acetate solution was dried over sodium sulfate and then concentrated down to a 20-ml volume by rotary evaporation. Each of two 0.1 ml aliquots (representing a total of 4.4. mg of starting material) was placed on a preparative TLC plate (silica gel) and developed with the solvent mixture n-hexane: ethyl acetate (3:2; v/v). The desired product was the fastest-running component ($R_f$ 0.70), which has a greenish-yellow color and is resolvable from the second component ($R_f$ 0.56) identified as 5-iodo-6-nitro-1,2-benzopyrone (yellow). The product was removed from the TLC plates and eluted from the silica gel with ethyl acetate, which was then removed by rotary evaporation. The dry residue was taken up in a minimal amount of warm methanol (0.5 ml), which upon cooling in the refrigerator resulted in the light greenish solid product (2 mg, 44% of theoretical yield), m.p. 175°–177° C. (with darkening). The mass spectrum showed its major high molecular weight peak at m/z 301; calculated for $C_9H_4INO_3$: 300.9236.

EXAMPLE 4

Preparation of Alkyl-5-Iodo-6-Amino 1,2-Benzopyrones and Alkyl-5-iodo-6-Nitros-1,2-Benzopyrones This example illustrates the preparation of alkyl-5-iodo-6-amino-1,2-benzopyrones and alkyl-5-iodo-6-nitroso-1,2-benzopyrones having 1–4 carbon atoms in the alkyl group.

Preparation of 7-methyl-5-iodo-6-amino-1,2-benzopyrone

To stirred solution of 3.20 g (0,020 mole) of commercially obtained 7-methyl-1,2-benzopyrone (7-methylcoumarin, Aldrich Chemical Co.) in 20 ml of glacial acetic acid cooled to 0° C. is added 2.0 ml of 1:1 (v/v) mixture of concentrated nitric acid and glacial acetic acid (*Indian J. Chem.*, 7:49 (1969)). After 2 hours at 0° C., the mixture is poured onto crushed ice, the precipitated nitration product is collected, washed with water and crystallized from ethanol. The purified product is then dissolved in 500 ml methanol and added to a stirred suspension of 0.50 g of 10% palladium catalyst on activated carbon in an aqueous solution of potassium borohydride (2.50 g, 0,046 mole) in 50 ml of water at room temperature. After 15 minutes, the mixture is filtered to remove the catalyst, and stripped of methanol/water by rotary evaporation. The dry residue as the amine free base is crystallized from ethanol resulting in 7-methyl-6-amino-1,2-benzopyrones (B).

The purified amine (I) is then redissolved in hot ethanol (125 ml at 60° C.) to which is added 3 ml of 2M hydrochloric acid and 1.95 g (0,012 mole) of iodine monochloride. After stirring at 60° C. for 15 minutes, the mixture is cooled and poured into a separatory funnel containing 175 ml of ethyl acetate, 125 ml of water and 6 ml of aqueous 2M sodium bisulfite (neutralized to pH 7.4), and the contents are vigorously mixed. Addition of more water (125 ml) gives rise to separation of phases, the organic (ethyl acetate) layer is isolated, washed with water, dried over sodium sulfate and stripped of solvent by rotary evaporation. The residue is taken up in a minimum amount of boiling hot ethanol, filtered and upon cooling the solution yields the crystalline iodinated product 7-methyl-5-iodo-6-amino-1,2-benzopyrone. Other alkyl 5-I-6-ABPs are prepared in the same way.

Alkyl-5-iodo-6-nitroso-1,2-benzopyrones may be prepared from above obtained alkyl-5-iodo-6-amino-1,2-benzopyrones by using the procedure described in Example 3.

EXAMPLE 5

Preparation of cycloalkyl-5-iodo-6-amino-1,2-benzopyrones

This example illustrates the preparation of cycloalkyl-5-iodo-6-amino-1,2-benzopyrones having 3–8 carbon atoms in the cycloalkyl group.

Preparation of
8-cyclohexyl-5-iodo-6-amino-1,2-benzopyrone

In 100 ml of benzene solvent, 10.2 g (0.050 mole) of synthetic 3-cyclohexyl-2-hydroxybenzaldehyde (*J. Chem. Soc. Perkin Trans. II,* 1862 (1980)) and ethoxy-carbonyl-methylene-triphenylphosphorane (0.075 mole) are refluxed for 24 hours employing a procedure described in *Synthesis,* 464 (1977), and the product 8-cyclohexyl-1,2-benzopyrone is purified by chromatography over silica gel using benzene as eluent. To a stirred solution of 4.56 g (0.020 mole) of 8-cyclohexyl-1,2-benzopyrone in 20 ml of glacial acetic acid, cooled to 0° C., is added 2.0 ml of a 1:1 (v/v) mixture of concentrated nitric acid and glacial acetic acid, and after 2 hours at 0° C., the mixture is poured onto crushed ice, the precipitated product collected on a filter, washed with water and crystallized from ethanol. The nitro-product is then dissolved in methanol (500 ml) and added to a stirred suspension of 0.50 g of 10% palladium catalyst on activated carbon in an aqueous solution of potassium borohydride (2.50 g, 0,046 mole) in 50 ml of water at room temperature. After 15 minutes, the reaction mixture is filtered, stripped of methanol/water by rotary evaporation, and the dry residue as the amine free base is crystallized from ethanol resulting in 8-cyclohexyl-6-amino-1,2-benzopyrone (B).

The purified amine (B) is then dissolved in ethanol (125 ml at 60° C.) to which is added 3 ml of 2M hydrochloric acid and 1.95 g (0,012 mole) of iodine monochloride. After stirring at 60 ° C. for 15 minutes, the mixture is cooled and poured into a separatory funnel containing 175 ml of ethyl acetate, 125 ml of water and 6 ml of aqueous 2M sodium bisulfite (pH 7.4), and the contents are vigorously mixed. Addition of more water (125 ml) gives rise to separation of phases, the organic (ethyl acetate) layer is isolated, washed with water, dried over sodium sulfate, and stripped of solvent by rotary evaporation. The residue is taken up in a minimum amount of boiling ethanol, filtered, and upon cooling the solution yields the crystalline iodo-product, 8-cyclohexyl-5-iodo-6-amino-1,2-benzopyrone (I).

Other cycloalkyl-5-I-6-ABPs may be prepared in the same manner.

Cycloalkyl-5-iodo-6-nitroso-1,2-benzopyrones may be prepared from above obtained cycloalkyl-5-iodo-6-amino-2-benzopyrones by using the procedure described in Example 3.

EXAMPLE 6

Preparation of
Phenyl-5-Iodo-6-Amino-1,2-Benzopyrones

This example illustrates the preparation of phenyl-5-iodo-6-amino-1,2-benzopyrones where phenyl may be unsubstituted or substituted.

Preparation of
3-phenyl-5-iodo-6-amino-1,2-benzopyrone

To a stirred solution of 2.38 g (0,010 mole) of synthetic 3-phenyl-6-amino-1,2-benzopyrone (*Kogyo Kagaku Zasshi,* 71:1010 (1968)) in 250 ml of ethanol at 60° C. is added 5 ml of 2M hydrochloric acid and 1.62 g (0.010 mole) of iodine monochloride. After 15 minutes, the mixture is cooled and transferred to a large separatory funnel containing 350 ml of ethyl acetate, 250 ml of water and 5 ml of 2M aqueous sodium bisulfite (pH 7.4). After vigorously mixing, addition of more water (250 ml) gives rise to separation of phases, and the upper organic phase is isolated, washed with water, dried over anhydrous sodium sulfate and stripped of solvent by rotary evaporation. The dried residue is then dissolved in a minimum amount of boiling hot ethanol, filtered and cooled, to give the crystalline iodo-product, 3-phenyl-5-iodo-6-amino-1,2-benzopyrone (I).

Other phenyl-5-I-6-ABPs may be prepared similarly. Phenyl-5-iodo-6-nitroso-1,2-benzopyrones may be prepared from above obtained phenyl-5-iodo-6-amino-1,2-benzopyrones by using the procedure described in Example 3.

EXAMPLE 7

Preparation of
Hydroxy-5-Iodo-6-Amino-1,2-Benzopyrones

This example illustrates the preparation of hydroxy-5-iodo-6-amino-1,2-benzopyrones.

4-hydroxy-5-iodo-6-amino-1,2-benzopyrone

To a stirred solution of 3.25 g (0,020 mole) of commercially obtained 4-hydroxy-1,2-benzopyrone (4-hydroxycoumarin, Aldrich Chemical Co.) in 20 ml of glacial acetic acid cooled to 0° C. is added 2.0 ml of a 1:1 (v/v) mixture of concentrated nitric acid and glacial acetic acid. After 1 hour at 0° C., the reaction mixture is poured onto crushed ice and the precipitated nitration product is collected on a filter, washed with water and crystallized from ethanol. The product is then dissolved in 500 ml methanol and added to a stirred suspension of 0.50 g of 10% palladium catalyst on carbon in an aqueous solution of potassium borohydride (2.50 g, 0.046 mole) in 50 ml of water at room temperature. After 15 minutes, the mixture is filtered to remove the catalyst, stripped of methanol/water by rotary evaporation, and the dry residue as the amine free base is crystallized from ethanol giving 4-hydroxy-6-amino-1,2-benzopyrone (B).

The purified amine is then dissolved in 125 ml of hot ethanol (60° C.) to which is added 2 ml of 2M hydrochloric acid and 0.65 g (0.004 mole) of iodine monochloride. After stirring at 60° C. for 15 minutes, the mixture is cooled and transferred to a separatory funnel containing 175 ml of ethyl acetate, 125 ml of water and 2 ml of aqueous 2M sodium bisulfite (pH 7.4), and the contents are vigorously mixed. Addition of more water (125 ml) gives separation of phases, and the organic (ethyl acetate) layer is isolated, washed with water, dried over anhydrous sodium sulfate and stripped of solvent by rotary evaporation. The dry residue is taken up in a minimum of hot ethanol, filtered, and upon cooling the solution yields the crystalline iodo-product. 4-hydroxy-5-iodo-6-amino-1,2-benzopyrone (I).

Other hydroxy-5-I-6-ABPs may be prepared in the same manner.

Hydroxy-5-iodo-6-nitroso-1,2-benzopyrones may be prepared from above obtained hydroxy-5-iodo-6-amino-1,2-benzopyrones by using the procedure described in Example 3.

EXAMPLE 8

Preparation of
Alkoxy-5-Iodo-6-Amino-1,2-Benzopyrones

This example illustrates the preparation of alkoxy-5-iodo-6-amino-1,2-benzopyrones.

Preparation of 4-methoxy-5-iodo-6-amino-1,2-benzopyrone

Using a methylation procedure described in *Synthesis* 144 (1978), to a stirred solution of 2.08 g (0.010 mole) of 4-hydroxy-6-nitro-1,2-benzopyrone, derived from the nitration of commercial 4-hydroxy-1,2-benzopyrone described in the Example 7, in 10 ml of anhydrous hexamethylphosphoramide (HMPA, Aldrich Chemical Co.), sodium hydride (0.24 g, 0.010 mole) is added at room temperature. After evolution of hydrogen gas is complete, dimethyl sulfate (1.51 g, 0.012 mole) in 5 ml of HMPA is added and the mixture is stirred for 1 hour and then transferred into a separatory funnel containing 100 ml of ethyl acetate. The organic layer is washed with 50 ml of 1M aqueous hydrochloric acid and then with a portion of water. After drying over sodium sulfate, the solvent is stripped off by rotary evaporation and the residue is dissolved and crystallized from hot ethanol. The methylated nitro-compound is then dissolved in methanol (500 ml) and reduced by adding it to a stirred suspension of 10% palladium catalyst on activated carbon in an aqueous solution of potassium borohydride (2.50 g, 0.046 mole) in 50 ml of water at room temperature. After 15 minutes, the mixture is filtered to remove the catalyst, stripped of solvent by rotary evaporation, and the dry residue as the amine free base crystallized from ethanol giving 4-methoxy-6-amino-1,2-benzopyrone (B).

The amine is then redissolved in hot ethanol 125 ml of ethanol at 60° C., to which is added 2 ml of 2M aqueous hydrochloric acid and 0.65 g (0.004 mole) of iodine monochloride. After stirring at 60° C. for 15 minutes, the mixture is cooled and transferred to a separatory funnel containing 175 ml of ethyl acetate, 125 of water and 2 ml of aqueous 2M sodium bisulfite (pH 7.4), and the contents are vigorously mixed. Addition of more water (125 ml) gives separation of phases, and the organic (ethyl acetate) layer is isolated, washed with water, dried over sodium sulfate, and stripped of solvent by rotary evaporation. The dry residue is taken up in a minimum of hot ethanol, filtered, and upon cooling the solution yields the crystalline iodo-product, 4-methoxy-5-iodo-6-amino-1,2-benzopyrone.

Other alkoxy-5-I-6-ABPs may be prepared in the same way.

Alkoxy-5-iodo-6-nitroso-1,2-benzopyrones may be prepared from above obtained alkoxy-5-iodo-6-amino-1,2-benzopyrones by using the procedure described in Example 3.

EXAMPLE 9

Preparation of Amino,5,Iodo-6-Amino-1,2-Benzopyrones

This example illustrates the preparation of amino-5-iodo-6-amino-1,2-benzopyrones.

Preparation of 5-iodo-3,6-diamino-1,2-benzopyrone

A solution of 2.06 g (0.010 mole) of synthetic 3-amino-6-nitro-1,2-benzopyrone (*Arch. Pharm.*, 296:365 (1963)) in 500 ml of methanol is added, at room temperature, to a stirred suspension of 0.50 g of 10% palladium catalyst on activated carbon in an aqueous solution of potassium borohydride (2.50 g, 0.046 mole) in 50 ml of water. After 15 minutes, the mixture is filtered to remove the catalyst, stripped of solvents by rotary evaporation, and the dry residue as amine free base crystallized from ethanol giving 3,6-diamino-1,2-benzopyrone (B).

The diamine is then redissolved in ethanol (125 ml at 60° C.) to which is added 2 ml of 2M aqueous hydrochloric acid and 0.65 g (0.004 mole) of iodine monochloride. After stirring at 60° C. for 15 minutes, the mixture is cooled and transferred to a separatory funnel containing 175 ml of ethyl acetate, 125 ml of water and 2 ml of aqueous 2M sodium bisulfite (pH 7.4), and the contents are vigorously mixed. Addition of more water (125 ml) gives separation of phases, and the organic (ethyl acetate) layer is isolated, washed with water, dried over sodium sulfate, and stripped of solvent by rotary evaporation. The dry residue is taken up in a minimum amount of hot ethanol, filtered, and upon cooling, the solution yields the crystalline iodo-product. 5-iodo-3-6-diamino-1,2-benzopyrone (I).

Other amino-5-I-6-ABPs are prepared in the same way.

Amino-5-iodo-6-nitroso-1,2-benzopyrones may be prepared from above obtained amino-5-iodo-6-amino-1,2-benzopyrones by using the procedure described in Example 3.

EXAMPLE 10

Preparation of halo-5-Iodo-Amino-1,2-Benzopyrones

This example illustrates the preparation of halo-5-iodo-6-amino-1,2-benzopyrones where halo may be fluoro, chloro or bromo.

Preparation of 3-fluoro-5-iodo-6-amino-1,2-benzopyrone

To a stirred solution of 3.28 g (0.020 mole) of synthetic 3-fluoro-1,2-benzopyrone (*J. Chem. Soc.*, 4033 (1961) in 20 ml of glacial acetic acid at 0° C. is added 2.0 ml of a 1:1 (v/v) mixture of concentrated nitric acid and glacial acetic acid. After 1 hour at 0° C., the reaction mixture is poured onto crushed ice and the precipitated nitration product is collected on a filter, washed with water and crystallized from ethanol. The product is then dissolved in methanol (500 ml) and added to a stirred suspension of 0.50 g of 10% palladium on activated carbon in an aqueous solution of potassium borohydride (2.50 g, 0.046 mole) in 50 ml of water at room temperature. After 15 minutes, the mixture is filtered to remove the catalyst, stripped of solvents by rotary evaporation, and the dry residue as the amine free base is crystallized from ethanol giving 3-fluoro-6-amino-1,2-benzopyrone (B).

The amine is then redissolved in (125 ml at 60° C.) to which is added 2 ml of 2M aqueous hydrochloric acid and 0.65 g (0,004 mole) of iodine monochloride. After stirring at 60° C. for 15 minutes, the mixture is cooled and transferred to a separatory funnel containing 175 ml of ethyl acetate, 125 ml of water and 2 ml of aqueous 2M sodium bisulfite (pH 7.4), and the contents are vigorously mixed. Addition of 125 ml water gives separation of phases, and the organic (ethyl acetate) layer is isolated, washed with water, dried over sodium sulfate, and stripped of solvent by rotary evaporation. The dry residue is taken up in a minimum amount of hot ethanol, filtered, and upon cooling the solution yields the crystalline iodo-product, 3-fluoro-5-iodo-6-amino-1,2-benzopyrone (I).

Other halo 5-I-6-ABP may be prepared in the same manner.

Fluoro-5-iodo-6-nitroso-1,2-benzopyrones may be prepared from above obtained fluoro-5-iodo-6-amino-1,2-benzopyrones by using the procedure described in Example 3.

In synthetic procedures for reduction of nitro-derivatives containing iodo or bromo substituents, sodium dithionite is substituted for potassium borohydride, since the latter reagent can displace these higher halogens from aromatic rings.

EXAMPLE 11

Cytostatic Effects of 5-I-6-ABP

This example illustrates effects of 6-amino-1,2-benzopyrone (6-ABP) and 5-iodo-6-amino-1,2-benzopyrone (5-I-6-ABP) on DNA synthesis in cultured cells.

In this study, the following cell lines were used. Cell line CG I, a non-tumorigenic hybrid of HeLa cells with normal human fibroblasts, and its tumorigenic revertant counterpart, CG1 III, as described in Science, 215:252 (1982). These cells were obtained from UC Irvine. 14C cells are EJ-ras transformed Rat-1 fibroblasts exhibiting steroid inducible enhancement of tumorigenicity as described in Proc. Natl. Acad. Sci., 84:1107 (1987). HEp-2 human epidermoid carcinoma cells were provided by Dr. L. Aurelian (University of Maryland). E-Ras cells were obtained from University of Cincinnati and represent an endothelial cell line transfected with pSV2neo plasmid as described in Proc. Natl. Acad. Sci., 76:1373 (1979). This cell line contains several copies of the activated human Ha-ras oncogene.

Cells were seeded to 2 cm$^2$ wells of Falcon tissue culture plates at a density of 6000±650 cells per well. Inhibitors were added to the seeding suspensions from stock solutions of 100 mM 6-ABP in water or 50 mM 5-I-6-ABP in dimethylsulfoxide (DMSO). DMSO alone at comparable concentration had no appreciable effect on DNA synthesis. Growth media were Dulbecco's MEM (lines #1 and 2), and Dulbecco's Modified Eagle's Medium (lines 3–6), containing 10% fetal bovine serum and penicillin (100 µg/ml) plus streptomycin (100 µg/ml). After incubation for 72 hours at 37° C. in a 5% $CO_2$ humidified atmosphere, incorporation of [$^3$H] deoxyadenosine (ICN, 18 Ci/mmol) into DNA was tested as follows: [$^3$H] deoxyadenosine (450,000 dpm in 40 µl ) of medium was added per well (each containing 600 µl of medium) and incubation at 37° C. was continued for 1 hour, followed by removal of the medium and rinsing of the wells 3 times with phosphate-buffered saline. Cells were then lysed in 500 µl of 0.06 M NaOH and the acid precipitable radioactivity was determined.

TABLE 1

| Cell Line | 6-ABP (0.5 mM) | % Inhibition 5-I-6-ABP (0.05 mM) |
| --- | --- | --- |
| 1. CG1 I | −19.8 (±13.3)% | −7.6 (±7.3)% |
| 2. CG1 III | −37.5 (±10.6)% | −64.4 (±10.7)% |
| 3. Rat −1 | −30.5 (±7.9)% | −35.6 (±2.0)% |
| 4. 14C | −53.3 (±6.6)% | −69.2 (±11.7)% |
| 5. HEp-2 | −47.6 (±9.9)% | −52.4 (±6.3)% |
| 6. E-Ras | −69.5 (±3.9)% | −81.8 (±3.9)% |

N=5; the results are expressed as percent inhibition relative to control cells.

The control cultures which were without drug treatment exhibited the following values of DNA-incorporated radioactivity (dpm per well):

CG1 I 13,050±2610;

CG1 III 22,560±4560;

Rat-1 7920±1,560;

14C 11,040±2,760;

HEp-2 18,750±4560;

E-Ras 27,255 3960.

Results of cell growth inhibition are shown in Table 1. In all cases, replication of particularly tumorigenic cell types is profoundly inhibited by 5-I-6-ABP treatment. In comparison 500 µM of 6-ABP had the same effectivity as 50 µM of 5-I-6-ABP.

EXAMPLE 12

Effectivity of 5-I-6-ABP Against HSV and CMV

This example illustrates the inhibitory activity of 5-I-6-ABP on HSV and CMV replication in a cell culture infected either with HSV or CMV.

Vero, HEp-2 or MRC-5 cells are exposed to various concentrations from 0.1 to 10mM of 5-I-6-ABP in various time intervals before infecting them with HSV-1 or HSV-2 (5–10 PFU/cell). Virus titers are determined 24 hours later.

5-iodo-6-amino-1,2-benzopyrones inhibit HSV and CMV growth. The inhibitory effect of 5-I-6-ABP is not affected by cell type.

The same studies as described above are performed using CMV infected cell culture. 5-I-6-ABP treatment also effectively inhibits CMV growth.

EXAMPLE 13

Direct Anti-HIV Effects of 5-I-6-ABP in Established Cell Lives in Culture

This example illustrates a direct inhibitory effect of 5-I-6-ABP on HIV replication in established cell cultures.

The effects of 5-I-6-ABP treatment of AA-2 and MT-2 cells was directly analyzed by cell count and viability tests including cloning efficiency and trypan blue uptake. The AA2 or MT-2 cell culture having initial cell count per well 0.5×10$^5$ was submitted to treatment with 3 mM of 6-ABP and or with 0.1 mM of 5-I-6-ABP and compared to untreated cell culture. The cells were counted 4 days after the treatment with 5-I-6-ABP and 6-ABP.

Viability test gave no evidence of toxic effects of 6-ABP. Results are shown in FIGS. 2 and 3 and were discussed previously.

It is evident that both 5-I-6-ABP and 6-ABP exert an inhibitory effect on cell proliferation. 5-I-6-ABP is 10 to 30 times more potent as an anti-HIV agent. Such inhibitory effect is temporary, reversible and coincidental with the complete abrogation of HIV replication. However, the slowing down of cell replication in AA-2 or MT-2 cells does not coincide with any detectable cellular. toxicity, a phenomenon that predicts a cytostatic anticancer effect of other drugs. This finding is unique, inasmuch as it does not involve cytotoxicity for either compound.

EXAMPLE 14

Inhibition of HIV Proliferation in Human Lymphoblasts

This example illustrates the inhibitory effect of 6-ABP on HIV proliferation in human lymphoblasts patients.

The HIV isolates used in these experiments are isolated from the blood of infected patients. After isolation, HIV infection is established in CEM cells, and these infected cells are used to produce a stock of HIV virus that is titered to measure the concentration of tissue culture infective doses (TCID).

5-I-6-ABP is dissolved in saline in an amount which is further diluted as required, and added to the culture medium containing cells at the predetermined concentrations.

Human peripheral blood mononuclear cells from a non-infected, normal individual are stimulated for 2 to 3 days with phytohemagglutinin in tissue culture, washed, aliquoted and cultured overnight with 200 TCID or 50 TCID of HIV and are either untreated or treated with 0.01, 0.1, 1.0 or 10.0 mM 5-I-6-ABP. The cells are placed in culture in medium containing IL-2, but in the absence of additional 5-I-6-ABP, and monitored at 6 days and 12 days for the production of HIV-p24 core antigen, or for measurements of particulate reverse transcriptase. A decrease in the amount of either of these indicators of HIV indicates an inhibition by 5-I-6-ABP in the ability of HIV to replicate in normal human lymphoblasts.

HIV p24 antigen is measured by ELISA, with a cutoff of 5 pgm/ml. Particulate reverse transcriptase is measured by centrifuging down free virus from tissue culture fluids, lysing HIV in a buffer containing detergent, magnesium, H3-labelled dTTP and poly rA.oligo dT primer, incubating for 1 hour, and measuring precipitable radioactivity, and is expressed as cpm per volume of HIV-containing medium.

The viability of lymphoblasts is measured by incubating the cells exposed to IL-2, HIV and to 6-ABP with H3-thymidine for 6 hours on the sixth day of culture and determining the amount of cpm incorporated per 100,000 cells placed in culture.

The inhibition of HIV which is observed following the 5-I-6-ABP treatment is temporary and reversible. Thus the antiproliferative effect of 6-ABP can be accomplished without detectable cell damage or death, in contrast to any of the currently employed or available cytostatic agents.

EXAMPLE 15

5-I-6-ABP Toxicity Studies

This example illustrates the lack of toxicity after intraperitoneal administration of 5-I-6-ABP to rats.

Toxicological tests administering 5-I-6-ABP to rats were performed under the following conditions.

Four Fisher 344/sim fBR male inbred rats (120–130 g. weight, Simonsen Laboratories, Inc., Gilroy, Calif.) were housed in plastic cages and received pelleted diet and water ad libitum. Two of 4 rats were injected (i.p.) with 5-I-6-ABP (100 mg/kg in DMSO) once a day for four consecutive days, and the other two rats received the same treatment except with lower dose of 5-I-6-ABP (59 mg/kg in DMSO). After four days of injection no apparent toxic effects have been observed. Chronic administration of 100 and 500 mg drug/kg continued for several weeks also did not show any toxic effects. In in vitro experiments, it was shown that at the concentration 100 mg/kg corresponding to 0.35 mM, the antiviral effect is maximal.

We claim:

1. A compound having the chemical formula:

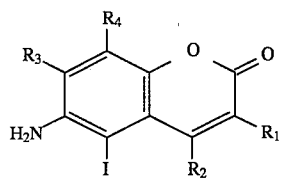

wherein $R_1$, $R_2$, $R_3$, or $R_4$ are each independently selected from the group consisting of hydrogen, hydroxy, amino, ($C_1$–$C_6$) alkyl, ($C_1$–$C_6$) alkoxy, ($C_3$–$C_7$) cycloalkyl, halo and phenyl and pharmaceutically acceptable salts thereof, wherein at least three of the four $R_1$, $R_2$, $R_3$, or $R_4$ substituents are always hydrogen.

2. The compound of claim 1, wherein $R_1$, $R_2$, $R_3$ and $R_4$ comprise hydrogen.

3. An antiviral composition, comprising the compound of claim 1; and a pharmaceutically-acceptable carrier.

4. A compound having the chemical formula:

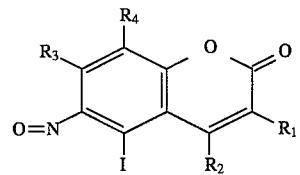

$R_1$, $R_2$, $R_3$, or $R_4$ are each independently selected from the group consisting of hydrogen, hydroxy, amino, ($C_1$–$C_6$) alkyl, ($C_1$–$C_6$) alkoxy, ($C_3$–$C_7$) cycloalkyl, halo and phenyl and pharmaceutically acceptable salts thereof, wherein at least three of the four $R_1$, $R_2$, $R_3$, or $R_4$ substituents are always hydrogen.

5. The compound of claim 4, wherein $R_1$, $R_2$, $R_3$ and $R_4$ comprise hydrogen.

6. An antiviral composition, comprising the compound of claim 4; and a pharmaceutically-acceptable carrier.

7. A compound of the chemical formula:

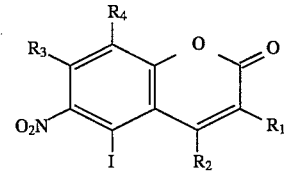

wherein $R_1$, $R_2$, $R_3$, or $R_4$, are each independently selected from the group consisting of hydrogen, hydroxy, amino, ($C_1$–$C_6$) alkyl, ($C_1$–$C_6$) alkoxy, ($C_3$–$C_7$) cycloalkyl, halo and phenyl, wherein at least three of the four $R_1$, $R_2$, $R_3$, and $R_4$ substituents are always hydrogen.

8. The compound of claim 7, wherein $R_1$, $R_2$, $R_3$, or $R_4$ are hydrogen.

9. A pharmaceutical formulation comprising the compounds of claims 7 or 8, and a pharmaceutically acceptable salt.

* * * * *

UNITED STATES PATENT AND TRADEMARK OFFICE
CERTIFICATE OF CORRECTION

PATENT NO. : 5,484,951

DATED : January 16, 1996

INVENTOR(S) : Kun et al.

It is certified that error appears in the above-indentified patent and that said Letters Patent is hereby corrected as shown below:

On the title page, item [54] and column 1, lines 2-4:

Please change the title to read: --5-IODO-6-AMINO-, 5-IODO-6-NITROSO- AND 5-IODO-6-NITRO-1,2-BENZOPYRONES USEFUL AS CYTOSTATIC AND ANTIVIRAL AGENTS--.

In the "OTHER PUBLICATIONS" section, the third reference should read: --Buki, K. et al., "Destabilization of $Zn^{2+}$ coordination in ADP-ribose transferase (polymerizing) by 6-nitroso-1,2-benzopyrone coincidental with inactivation of the polymerase but not the DNA binding function," *FEBS Lett.* 290:181-185(1991).

In the ABSTRACT, first line, "benopy" should read --benzopy--.

In FIG. 2, in the legend, "LODO-ABP(100umol) d4" should read --IODO-6-ABP(100umol) d4--.

In FIG. 3, in the legend, "LODO-6-ABP(100umol) d4" should read --IODO-6-ABP(100umol) d4--.

Column 4, line 23, "6-amino-benzopyrone" should read --6-amino-1,2-benzopyrone--.

Column 9, line 61 and Column 11, line 45, "dithionate" should read --dithionite--.

Column 23, line 28, please delete "hot ethanol".

Signed and Sealed this

Eleventh Day of June, 1996

Attest:

BRUCE LEHMAN

Attesting Officer

Commissioner of Patents and Trademarks